(12) United States Patent
Gelardi

(10) Patent No.: US 10,982,899 B1
(45) Date of Patent: Apr. 20, 2021

(54) ESSENTIAL OIL MANUFACTURING

(71) Applicant: Paul Joseph Gelardi, Biddeford, ME (US)

(72) Inventor: Paul Joseph Gelardi, Biddeford, ME (US)

( * ) Notice: Subject to any disclaimer, the term of this patent is extended or adjusted under 35 U.S.C. 154(b) by 751 days.

(21) Appl. No.: 15/592,299

(22) Filed: May 11, 2017

Related U.S. Application Data

(60) Provisional application No. 62/334,650, filed on May 11, 2016, provisional application No. 62/343,907, filed on Jun. 1, 2016.

(51) Int. Cl.
| | | |
|---|---|---|
| *F26B 5/06* | (2006.01) | |
| *B01D 11/02* | (2006.01) | |
| *B01D 8/00* | (2006.01) | |
| *B01D 3/14* | (2006.01) | |
| *B01D 45/16* | (2006.01) | |
| *B01D 46/00* | (2006.01) | |
| *B01D 50/00* | (2006.01) | |
| *B01D 53/26* | (2006.01) | |
| *A61K 36/185* | (2006.01) | |
| *B65B 3/04* | (2006.01) | |
| *B65C 3/06* | (2006.01) | |

(52) U.S. Cl.
CPC ............. *F26B 5/06* (2013.01); *A61K 36/185* (2013.01); *B01D 3/14* (2013.01); *B01D 8/00* (2013.01); *B01D 11/0203* (2013.01); *B01D 45/16* (2013.01); *B01D 46/003* (2013.01); *B01D 50/002* (2013.01); *B01D 53/26* (2013.01); *B65B 3/04* (2013.01); *B65C 3/06* (2013.01); *A61K 2236/10* (2013.01); *A61K 2236/37* (2013.01); *A61K 2236/39* (2013.01)

(58) Field of Classification Search
None
See application file for complete search history.

(56) References Cited

U.S. PATENT DOCUMENTS

2010/0119606 A1* 5/2010 Whittle .............. B01D 11/0242
424/484

* cited by examiner

*Primary Examiner* — Michael Barker
(74) *Attorney, Agent, or Firm* — James Creighton Wray

(57) ABSTRACT

Botanical materials are dehydrated, ruptured and comminuted into particles by blades or whips in a fluidized bed. Particles separated from a drying gas are transferred to reduced pressure insulated vessels. Solvents dissolve components of the particles under precise temperature control. Solvents are recirculated and distilled to recover distillates. Distillates are refined by thermal and pressure changes to remove fats, waxes and contaminants and are fractionated to specific essential oils. The essential oils are tested, winterized, filtered, decarboxilated, polished, diluted and discharged into collection vessels. The collected essential oils are pumped through needles into sealed cartridges. The cartridges are tamper-proofed, printed and labeled with batch, botanical source, process, tracking and tracing information and codes.

9 Claims, 32 Drawing Sheets

HIGH TECH EXTRACTORY

| MATERIAL PREP | EXTRACTION | REFINING | FINISHING |
|---|---|---|---|
| SUBSYSTEM 1<br>AUTOMATIC INCOMING CONVEYOR | SUBSYSTEM 2<br>AUTOMATIC LOADING INFEED / OUTFEED | SUBSYSTEM 3<br>CARTRIDGES / OUTFEED CONVEYER | SUBSYSTEM 4<br>INTERVAL INFEED |
| EXTRACTION PREP MODULE<br>• SHRED<br>• DRY<br>• DECARBOXYLATE (OPTION)<br>• GRIND<br>• PACK | EXTRACTION MODULE<br>• AUTOMATIC LOADING AND UNLOADING<br>• EXTRACTION MODULE<br>• OUTFEED MODULE (BEAKERS) | CONDITIONING & TRANSPORT MODULE<br>• FREEZE<br>• FILTER<br>• DISTILL<br>• DECARBOXYLATE (OPTION)<br>• DILUTE<br>• OUTFEED MODULE (INPROCESS CONTAINER) | FINISHING MODULE<br>• INTERNAL INFEED<br>• FILLING<br>• STOPPERING<br>• MOUTHPIECE<br>• LABEL<br>• INJECT INTO OUTER PACKAGE<br>• PRINT & APPLY PRODUCT INFORMATION LABEL |

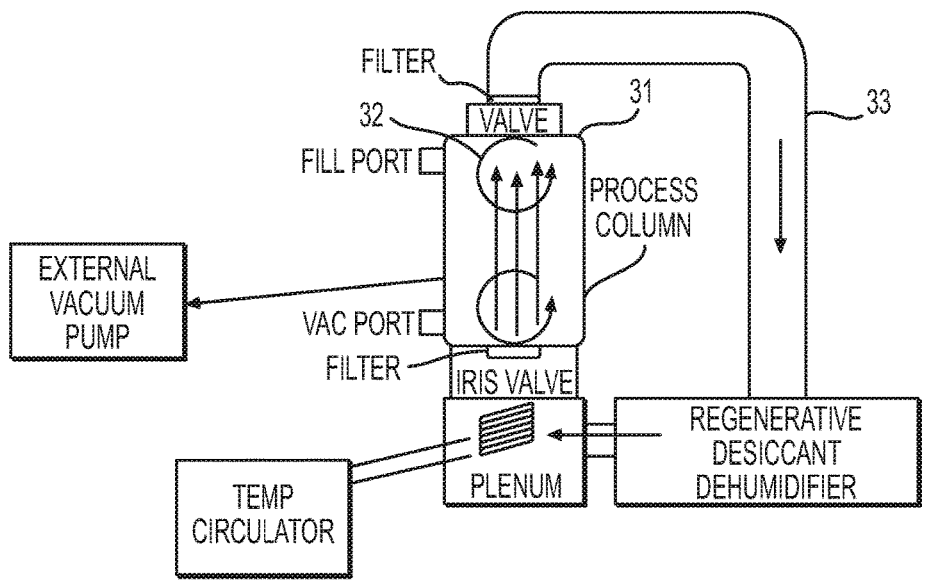

*FIG. 3*

SIEVING FILTERS & PARTICLE COLLECTION
W/ FILTER CLEARING DEVICES

FILLING OF VAPOR CARTRIDGES
AKA CARTOMIZERS & CLEAROMISERS

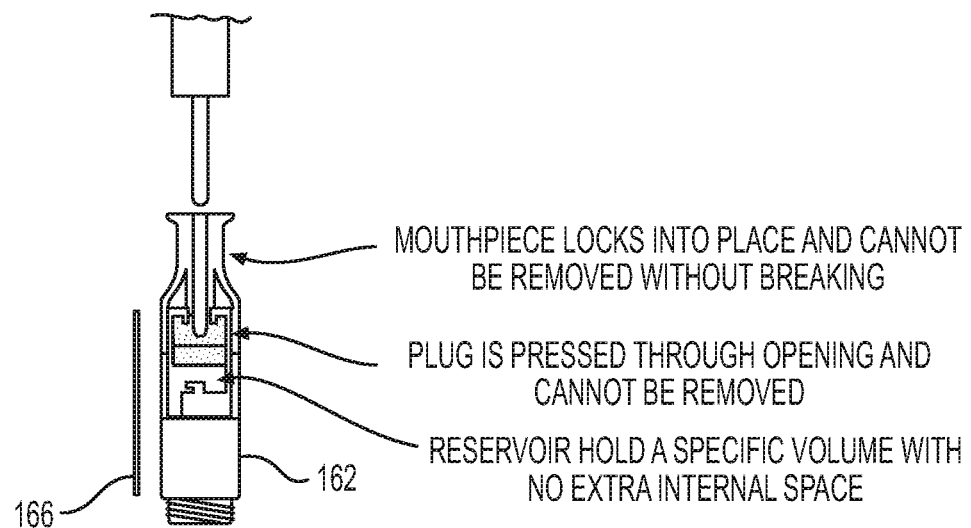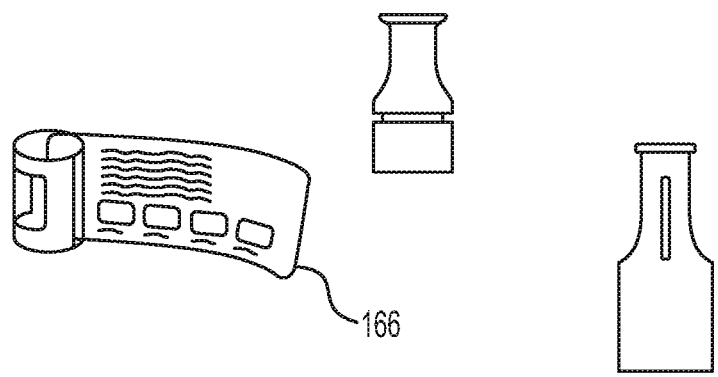
FIG. 22

Vapor Cartridge Mark10 Rev 0

FIG. 35 SECTION A-A

FIG. 38 SECTION B-B

ESSENTIAL OIL MANUFACTURING

This application claims the benefit of U.S. Provisional Application No. 62/334,650 filed May 11, 2016 and Provisional Application No. 62/343,907 filed Jun. 1, 2016, which are hereby incorporated by reference in their entirety as if fully set forth herein.

BACKGROUND OF THE INVENTION

Summary of Current Practices
Typical Process

The complete $CO_2$ Supercritical Fluid Extraction process (SFE) for extracting essential oils from botanical material for use in edible, vaporized or topical products is typically as follows.

Harvest crop,
Dry,
Decarboxylate. This is an optional step. Some processes decarboxylate the dried, raw plant material before extraction, others decarboxolate after extraction.
Trim and grind,
Pack into an SFE extraction vessel,
Perform $CO_2$ Supercritical Fluid Extraction using heat and pressure in the form of a supercritical fluid, to extract desired substances from the material and collect them in a container,
Dilute extract with an alcohol such as ethanol,
"Winterize" the extract solution chilling it to a temperature below 0° C.; preferably –15° C. to –25 C for 24 to 54 hours. This results in a slurry,
Filter slurry to remove waxes and impurities,
Distill filtered solution. This produces an oil commonly referred to as "honey oil",
Decarboxylate the honey oil. Cannabis oils are typically de-carboxylated at approximately 120° C., and
The de-carboxylated oil may be further refined using vacuum and filtering techniques sometimes referred to as "polishing".

Optional Finishing Processes for Vaporizers

The polished oil is used as a concentrate for edibles, topical creams, or oil vaporizers, or it is further heated and dried to create a solid material for solid vaporization.

For oil vaporization, the polished oil is often diluted with polyethylene glycol (PEG), polypropylene glycol, vegetable glycerin, cannabis terpenes, or a combination thereof to achieve the appropriate viscosity and desired performance for the chosen vaporizer.

Shortcomings of the Current Practices

The SFE process yields a higher quality extract than other extraction methods, because SFE can be selectively tuned through heat and pressure to extract desired substances selectively and without leaving any harmful residual solvents. SFE is, however, a time and labor consuming process yielding variable results. This is partially due to the volatility of certain bio-botanicals such as cannabis whose properties and chemical makeup change with time and environmental conditions. The variability is also due to the variability of the multistep manual nature of the current process.

The variability leads to uncertain results for consumers. While variability may be acceptable to some people, medical marijuana patients and sophisticated recreational users need, or should be able to obtain, reliably consistent and predictable effects.

The material preparation phase of production includes trimming, drying, and grinding.

1. Nutrient rich plant parts are trimmed and separated from low nutrient parts like stalks, stems and roots to improve the efficiency of later operations. This is done by hand or with automated trimmers.
2. Drying removes water in order to prevent material degradation from natural causes, (e.g. mold), and to aid in the extraction process. Water content in the material interferes with and slows down the extraction process.
   a. Dehydration is performed by circulating air, especially dry air, at elevated temperatures over and around materials. This is an ancient method that is slow, inconsistent, unreliable, subject to ambient environmental conditions and prone to developing mold.
   b. Freeze drying is an excellent method that preserves nutrient value, but is both capital and energy intensive making it unaffordable for many products.
   c. Microwave drying is widely used for many food applications, but relies on heat created by the microwaves to dry materials. The heat created results in lower nutrient preservation.
   d. Fluid bed drying is extensively used in the pharmaceutical and nutraceutical industries, but it requires elevated temperatures at atmospheric pressure to dry resulting in significant losses in nutrient values.

Current Fractionation Methods

The current methods of fractionating extract are:
Process the material at a high pressure and temperature, then separate the resultant mixed molecular weight through use of two or more separator vessels set at varying pressure drops.
Employ in-line gas chromatography to evaluate and direct the extract analytes at the particle level into collection vessels.
Employ in-line gas chromatography to characterize extraction profiles for use in a later purification process.

In practice, especially for certain botanicals like cannabis, none of these types of fractionation have been commercially successful other than for laboratory scale applications. In the first case, the mixed molecular weight extract tends to stick together and are not effectively separated by means of a pressure drop because the different molecular weight materials are cohesive, stick to each other, do not "pull apart from each other", and do not drop neatly into different separation vessels.

In the second case, while the extracts may be selectively extracted by a series of extract pressure and temperature fractionation steps, they are not separated from each other between process steps, subsequently mix together within the system, and therefore are not separated neatly before being directed to a series of collection vessels. Also, particle-level fractionation is a slow and expensive method. It is not suited to production extraction because the subject flow of extract is a mixture of analytes and a tangle of material with cohesive properties not easily fractionated at production speeds.

In the third case, the method is intended as a first step before purification of a target analyte in a subsequent.

Needs exist for better essential oil manufacturing.

Cannabis Authenticate Track & Trace Methods

There exist systems for tracking cannabis from seed to sale by use of cultivation lot numbers, radio frequency tags and/or barcodes. There exist systems for the collection of information about relevant grow information associated with plant material from cultivation lot numbers. The lot information, which will be referred to as its bio-history, can include among other things: its DNA, genetic history, nutrient feeding history, spectral energy exposure, as well as test data on contaminants and cannabinoid levels.

The effects of cannabinoids on humans, and other animals, are highly complex and personal in nature. Each human has their own unique endo-cannabinoid system, personal endo-cannabinoid profile and, cannabinoid receptors in the brain that respond uniquely when supplemented by ingestion of phyto-cannabinoids from cannabis. The cannabinoid receptors are involved in a wide range of physiological processes. There are some researchers who suggest that who we are as humans both physically and mentally is largely influenced by our endo-cannabinoid system.

The active compounds in cannabis are phyto-cannabinoids. By some accounts there are over 100 different phyto-cannabinoids present in varying amounts within cannabis plants. Each phyto-cannabinoid has different effects on humans, and these effects work in concert with each other in what is referred to as the entourage effect. Each cultivation lot of cannabis has a unique phyto-cannabinoid profile based upon the strain of the plant and its bio-history.

To add to the complexity, immediately after harvest the phyto-cannabinoid profile begins to change due to exposure from post-harvest spectral energy of all kinds, environmental conditions, and time. The method used to prepare cannabis products for use and the method of ingestion also affect: the cannabinoids delivered to the patient/consumer, the amounts of each absorbed, the rate of absorption and ultimately, its effects on the patient/consumer's experience. In addition, these effects can be affected by other drug interactions.

There is currently no system that effectively prescribes strains, or lots of cannabis, to patient/consumers. This leaves the patient/consumer to manage their own selection of products to use, method of ingestion and dosage amount. For a patient/consumer to get the desired effects, reference information is needed.

There is currently no system that allows patients/consumers easy access to that information, nor any system that allows them to read and/or share testimonials on their experiences and easily track their experience in a journal.

In addition, there is also need for a way for patient/consumers and regulatory agencies to: authenticate, track and trace products containing essential oil products from seed all the way to individually packaged products and; a method of reliably dosing essential oils and extracts into vaporized, edible and topical products.

SUMMARY OF THE INVENTION

The Hightech Extractory System (HES) is a novel process for bio-botanical extraction comprised of a suite of system modules, which are designed to improve, automate and integrate the manufacturing process from source bio-botanical material to packaged oils, as well as, edible, vaporized, or topical products.

HES separates the process into five subsystem modules that include: material preparation, essential oil extraction, essential oil refining, filling/dispensing & packaging, and process control & documentation.

New features include, among others:

an apparatus and method for integration of a freeze drying process with a fluidized bed, an apparatus and method for the combination of vaporization and sublimation drying in a single vessel, an apparatus and method for the rupturing of the cell structure of materials using freezing, drying and sublimation process cycles to increase the porosity of the material, so as to increase extraction yields and to decrease extraction time, an apparatus and method for automated grinding and sieving within a drying vessel, an apparatus and method for an automated process to shred, dry, grind and/or sieve bio-botanical materials, a method to characterize the extraction process of a specific material through a Design Organization of Experiments (DOE) process to more effectively extract materials and yield desired compounds in less time with fewer contaminants, a method to fractionate extracts into compounds by use of a programmed process sequence, a method to improve the fractionation of extracts into compounds within a $CO_2$ Supercritical Fluid Extraction process (SFE) through the use of a pump, piping and flushing material, an apparatus and method for the use of a flushing solvent that is also used as the solvent for the "winterization" of extracted oils so as to remove fats and waxes from the extract, an apparatus and method for removing fats, waxes and contaminants from unrefined extracted oils, an apparatus and method for distilling and refining essential oils, an apparatus and method or decarboxylating essential oils, an apparatus and method for diluting extracts, an apparatus and method that includes one or more of the above 4 process steps, an apparatus and method for filling empty fully assembled cartridges, an apparatus and method for dispensing into recipes of edible products, a method for integrating authenticate, track and trace database systems with data from filling and cartridge labeling processes, a method for labeling a vaporizer cartridge to provide tamper evidence, a method for labeling vaporizer cartridges, edible products and topical products with content information for users, a method for labeling a vaporizer cartridge with authenticate, track and trace information, a method for authorizing the filling of cartridges, a method for authorizing the use of filled cartridges, and a method of allowing patient/consumer access to authenticate, track and trace information, production lot data, cannabinoid profiles and empirical patient/consumer reviews and testimonials.

These and further and other objects and features of the invention are apparent in the disclosure, which includes the above and ongoing written specification, with the claims and the drawings.

BRIEF DESCRIPTION OF THE DRAWINGS

FIG. 2 is another schematic representation of the new High Tech Extractory.

FIG. 3 is a schematic representation of a Cryo-Bed™ vessel.

FIG. 22 shows vapor cartridge loading and labeling.
FIG. 35 is a cross-sections view of the vapor cartridge taken along line A-A of FIG. 34.
FIG. 38 is a cross-sectional elevation of the vapor cartridge taken along line B-B in FIG. 37.

DETAILED DESCRIPTION

The Hightech Extractory System

The Hightech Extractory System (HES) 10 is a botanical oil "plant to package" system. The integrated suite of systems and modules improve, automate and integrate steps in the manufacture of bio-botanical oils, vaporizers and edible products from source material to packaged products. HES is used to:
reduce manufacturing time,
reduce labor,
reduce variability,
maximize retention and extraction of desired substances,
improve long term stability of extracted materials,
maximize the return on capital,
reduce waste,
improve quality,
allow for precise monitoring, control and documentation of the process and product, and facilitate integration of authenticate, track and trace databases into useful and cost effective tools for process and product optimization, as well as, for consumer protection and regulatory compliance.

The extract concentrate manufacturing process includes trimming, drying, grinding, extraction, winterization, distillation, decarboxylation, polishing, dilution, cartridge filling, and dispensing into edible or topical product manufacturing processes.

The typical botanical vape cartridge manufacturing process is comprised of trimming, drying, grinding, extraction, winterization, distillation, decarboxylation, polishing, cartridge filling, cartridge assembly and packaging (not necessarily in that order).

Figure 1:
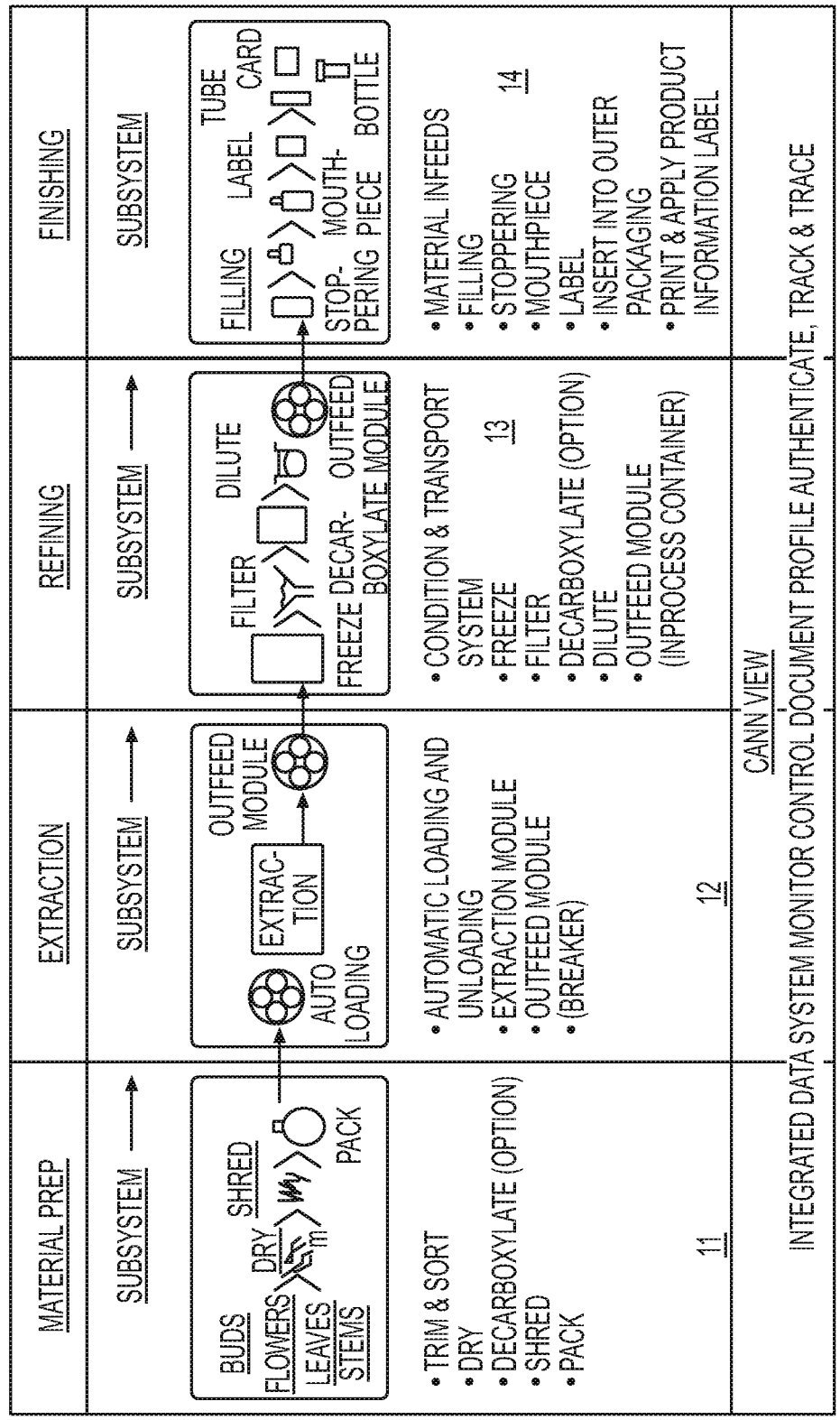
FIG. 1 is a schematic representation of the new High Tech Extractory.

HES groups these operations into five sub-systems:
1. CryoCure™ Material Preparation,
2. improved Supercritical Fluid Extraction System,
3. botanical Oil Refining System,
4. filling/Dispensing and Labeling System, and
5. process Control, Optimization and Documentation, An extractory system 10 shown in FIG. 1 has subsections for material preparation 11, extraction 12, refining 13 and finishing 14.

Another representation of the extractory system 10 is shown in FIG. 2. The CryoCure™ driving, grinding and separation shows material preparation 1, extraction 2 refining 3 and finishing 4.

CryoCure© Drying, Grinding and Sieving System
Raw Material Preparation
The HES Cryocure™ System The HES CryoCure™ System is a novel, cryogenic drying process that incorporates elements of freeze drying and fluidized bed drying in order to maximize nutrient retention, speed the extraction rate and reduce the capital and processing costs of drying bio-botanical materials. The system can also be configured to incorporate "cryo-grinding" of the material and automated sieving to yield high-quality, finely-ground material within a single integrated process. It can do so while the material is in a dehydrated state. It can maintain this state until the material is loaded into hermetically-sealed containers to further prolong preservation.

Essential oils can be more easily extracted from bio-botanical materials if the cell walls of the materials can be first ruptured. This can be done with freeze drying. However, freeze drying processes are typically based on minimizing cell wall damage so as to enhance appearance features (i.e. keeping a dried fruit looking like that fruit), therefore materials are typically "flash" frozen to minimize the size of the water crystals formed and to minimize the size of subsequent channels that are formed during partial pressure sublimation and second stage drying.

Because the CryoCure System™ is intended as material preparation for supercritical fluid extraction, substrate appearance doesn't matter. What matters is enhancing the extraction process by removing water, creating porosity, and reduction of the substance particle size to maximize surface area. The CryoCure System™ achieves this through "cryo-cracking", cryo-convection" and "cryo-grinding". Though these steps can be performed separately, a better method is to combine the steps into a single system to reduce costs and maintain better control over the process.

Cryo-Cracking

In the cryo-cracking process, the substrate material is frozen in order to rupture call walls in the material, then dehydrated in a drying vessel, such as a process column, using a combination of convective, radiant, and conductive heat, combined with convective gas flow and/or a partial pressure to effect evaporative and sublimation drying, aka desiccation. The cryo-cracking process can be made more effective by slowly freezing the material so as to maximize water crystal size and maximize the size of subsequent cell wall ruptures and channel size.

Cryo-cracking elements are shown in FIG. 3 with a drying and grinding process column 31. Grinding whips 32 and a water removal column 33 use a high velocity gas just above the water freezing temperature.

Figure 4:
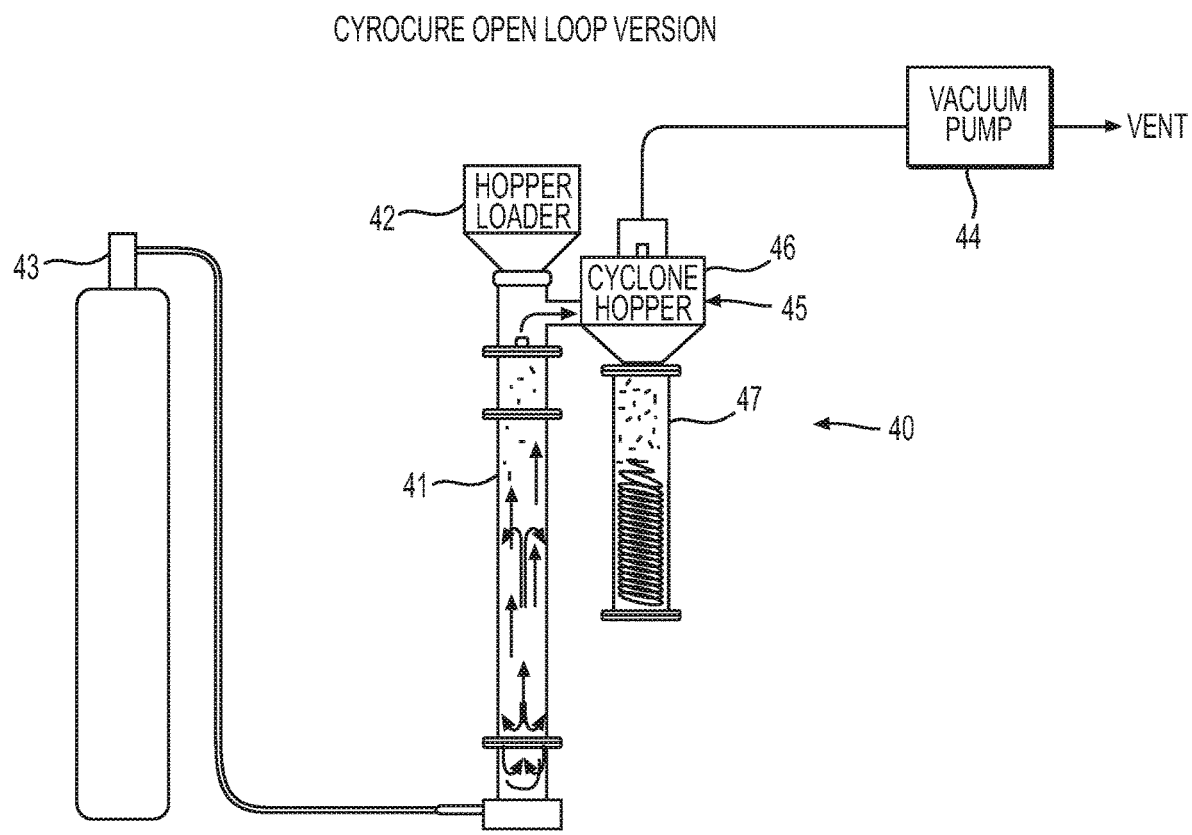
FIG. 4 is a schematic representation of a Cryocure™ Open Loop version.

A CryoCure™ open loop version 40 in FIG. 4 has a freezing and sublimation column 41 with a hopper loader 42 and a liquid nitrogen or carbon dioxide feed 43. A vacuum pump 44 and a cyclone separator 45 with a trapping filter 46 drop particles into the collection canister 47.

Figure 5:
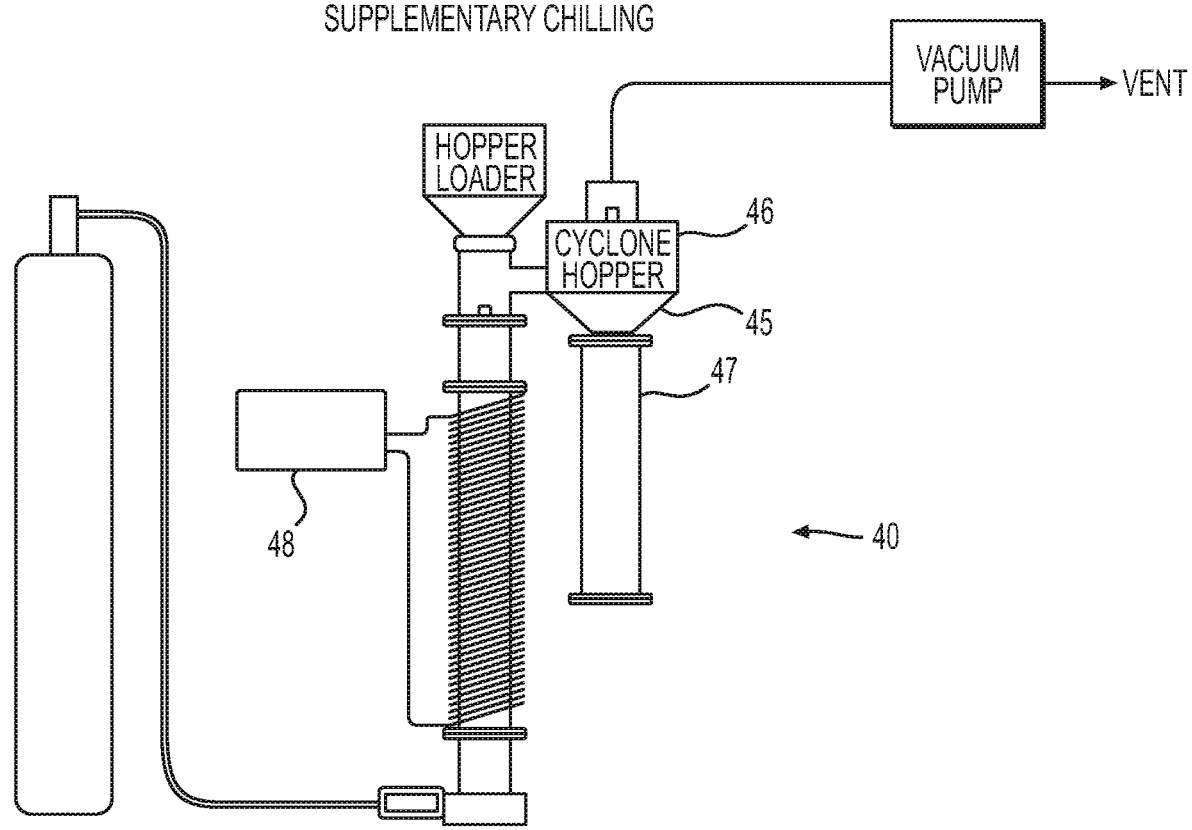
FIGS. 5 and 6 are schematic representations of Cryocure™ Open Loop version with supplementary chilling.

The same system 40 is shown with a supplementary chilling 48 in FIG. 5.

Figure 6:
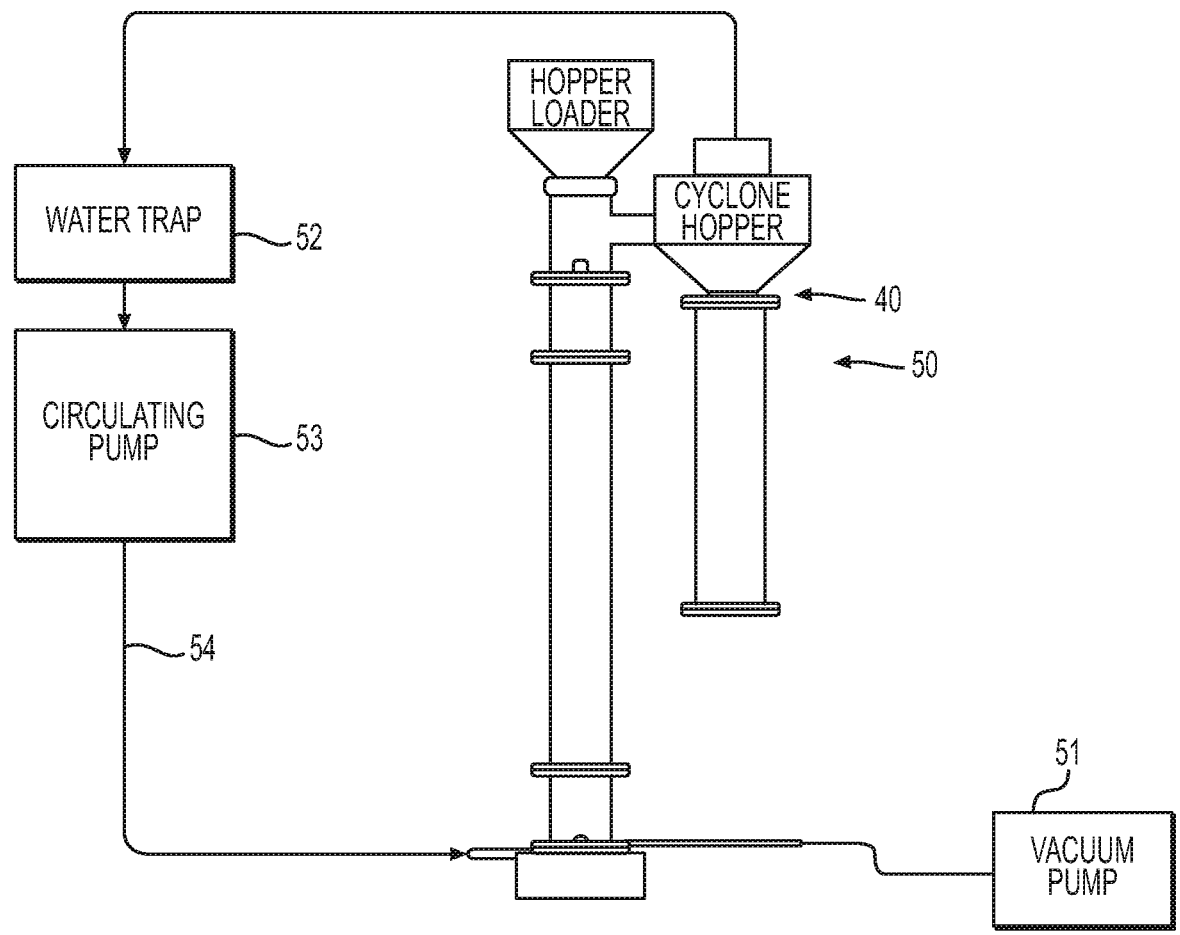

FIG. 6 shows the system 40 modified 50 with a vacuum pump 51 and water trap 52 and circulating pump 53 in a circulating loop 54.

Figure 7:
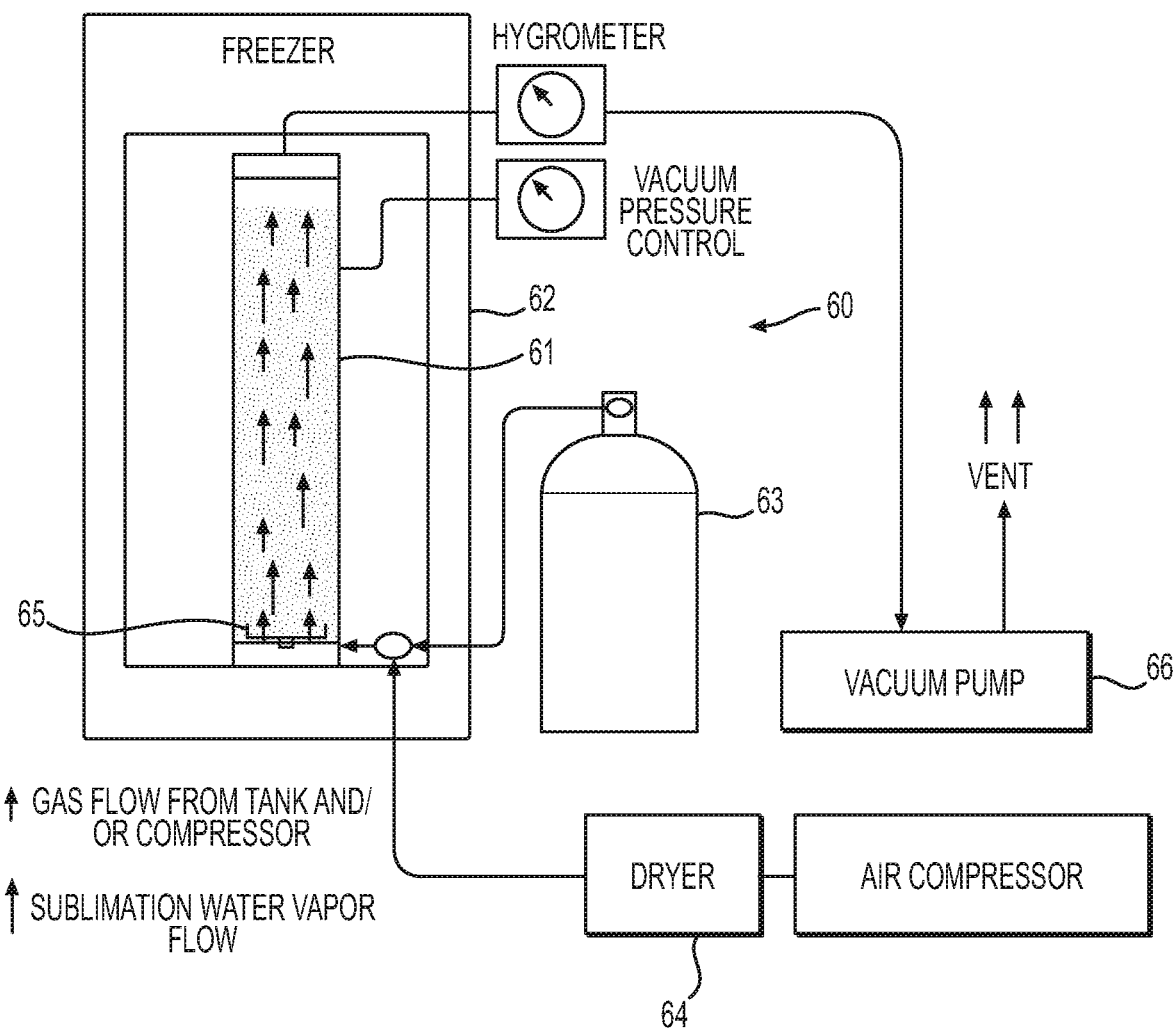
FIG. 7 is a schematic representation of Cryocure Freeze Sublimation Dry Grind.

FIG. 7 shows CryoCure™ freezing 60 with the process column 61 in the freezer 62. A liquid nitrogen source 63 and compressor and dryer 64 circulate gas through a grinder 65. A vacuum pump 66 and a vacuum pressure control and hygrometer ensure proper conditions within the column.

Figure 8:
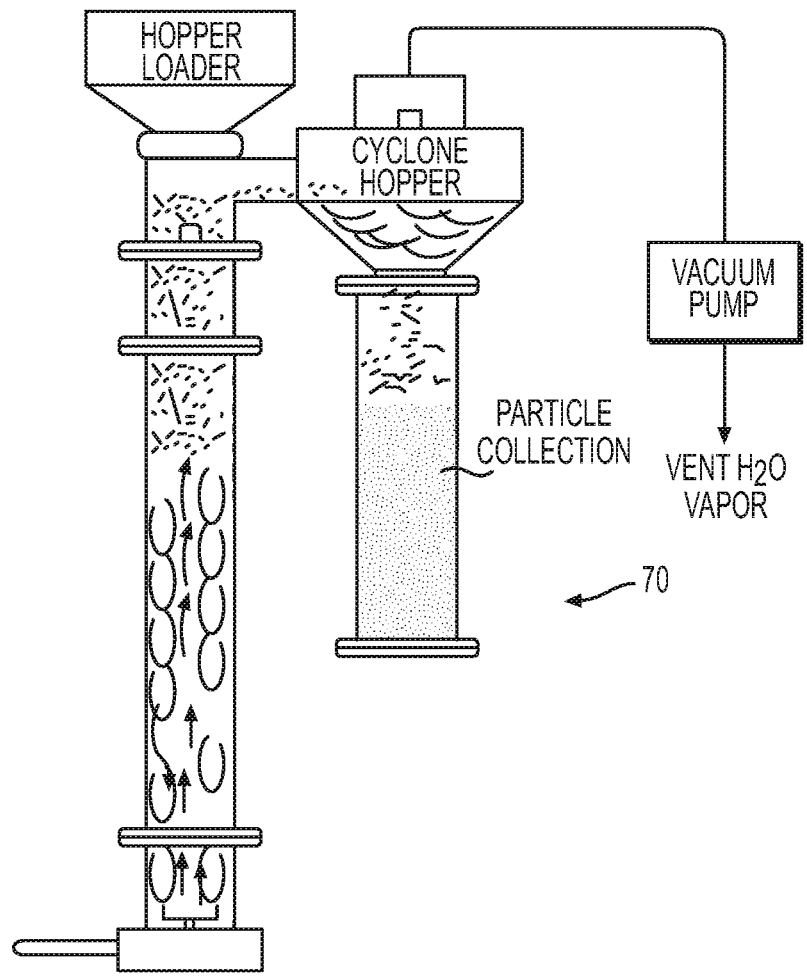
FIG. 8 is a schematic representation of a new Cryocure.

FIG. 8 shows a closed loop version 70 similar to the open loop version shown in FIG. 4.

Figure 9:
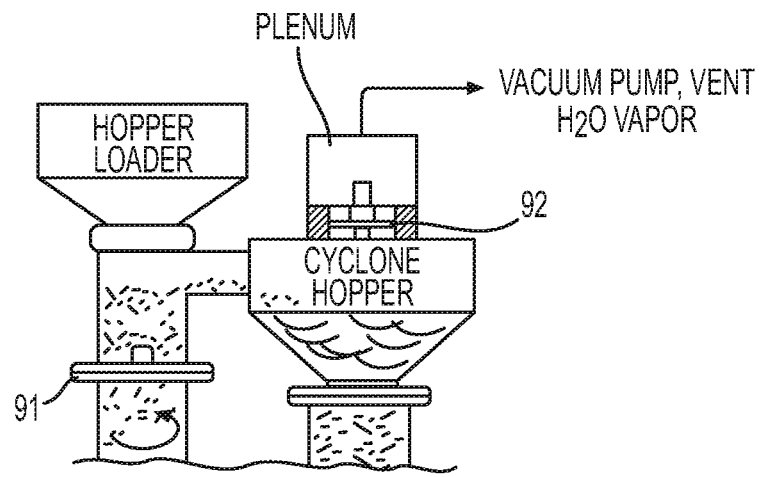
FIG. 9 shows filters and particle collection.

FIG. 9 shows details of the closed loop and open loop versions with pass through filter 91 and no pass filter 92. Filter disc cleaning devices 93 are used in both filters.

Figure 10:
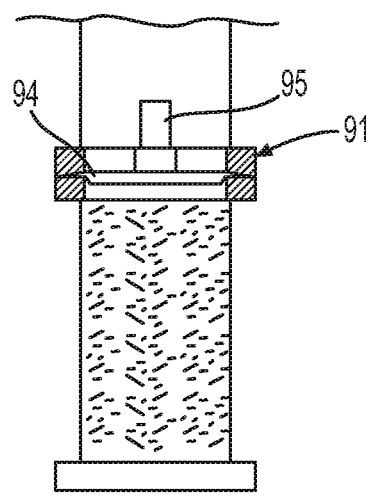
FIG. 10 shows a filter with vibrating and clearing.

FIG. 10 is a detail of the pass through filter 91 and vibrating cleaning device 94 with a drive motor 95.

Figure 11:
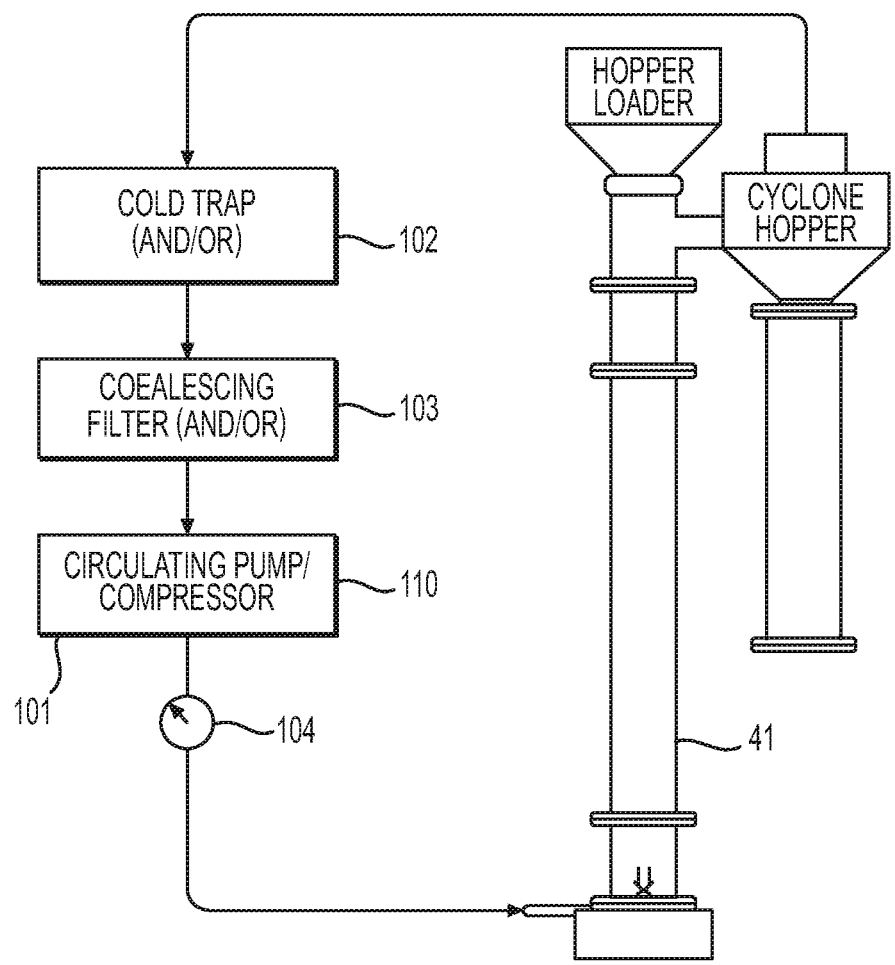
FIG. 11 schematically shows a closed loop system.
Figure 12:
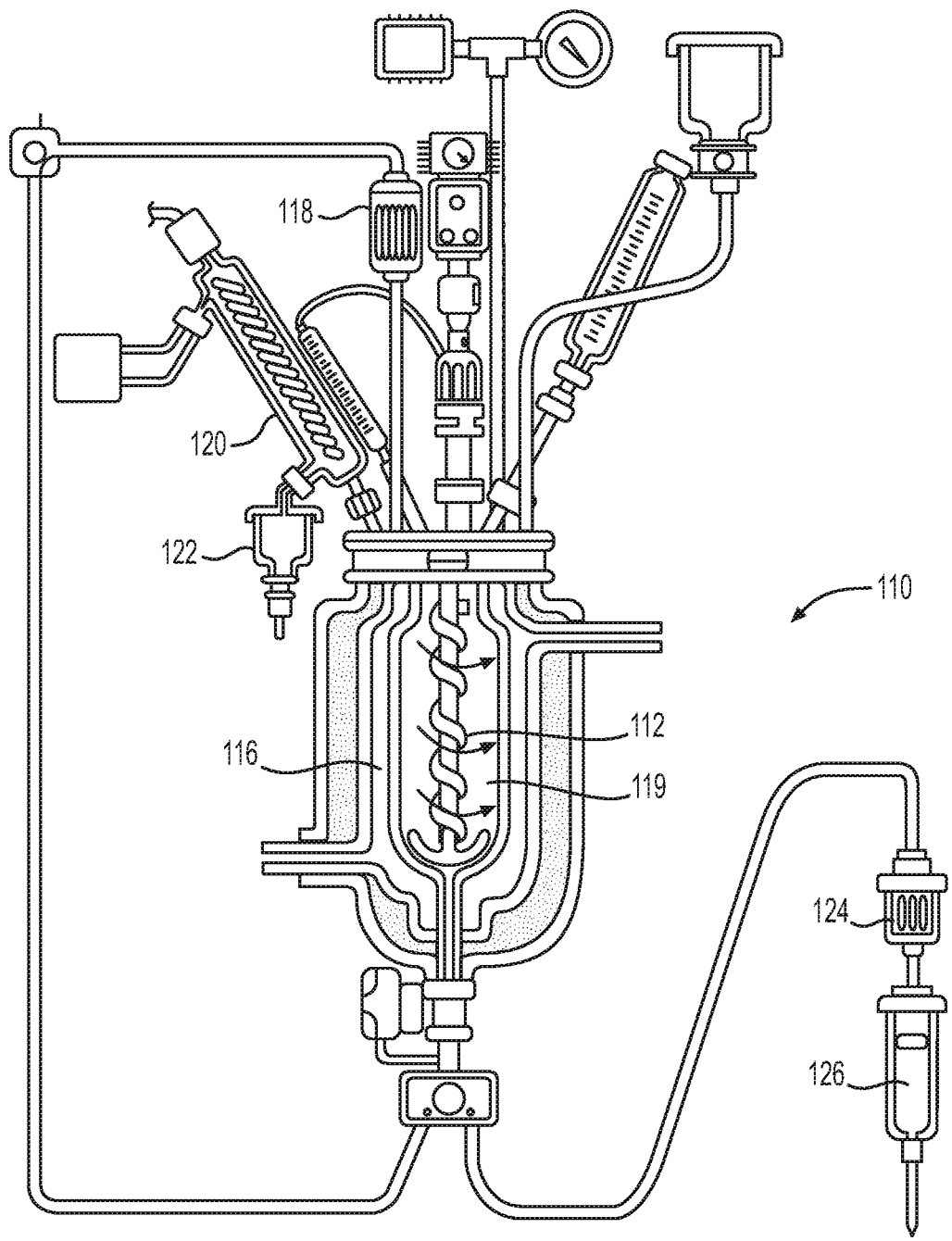
FIGS. 12-19 show oil refining steps.
Figure 13:
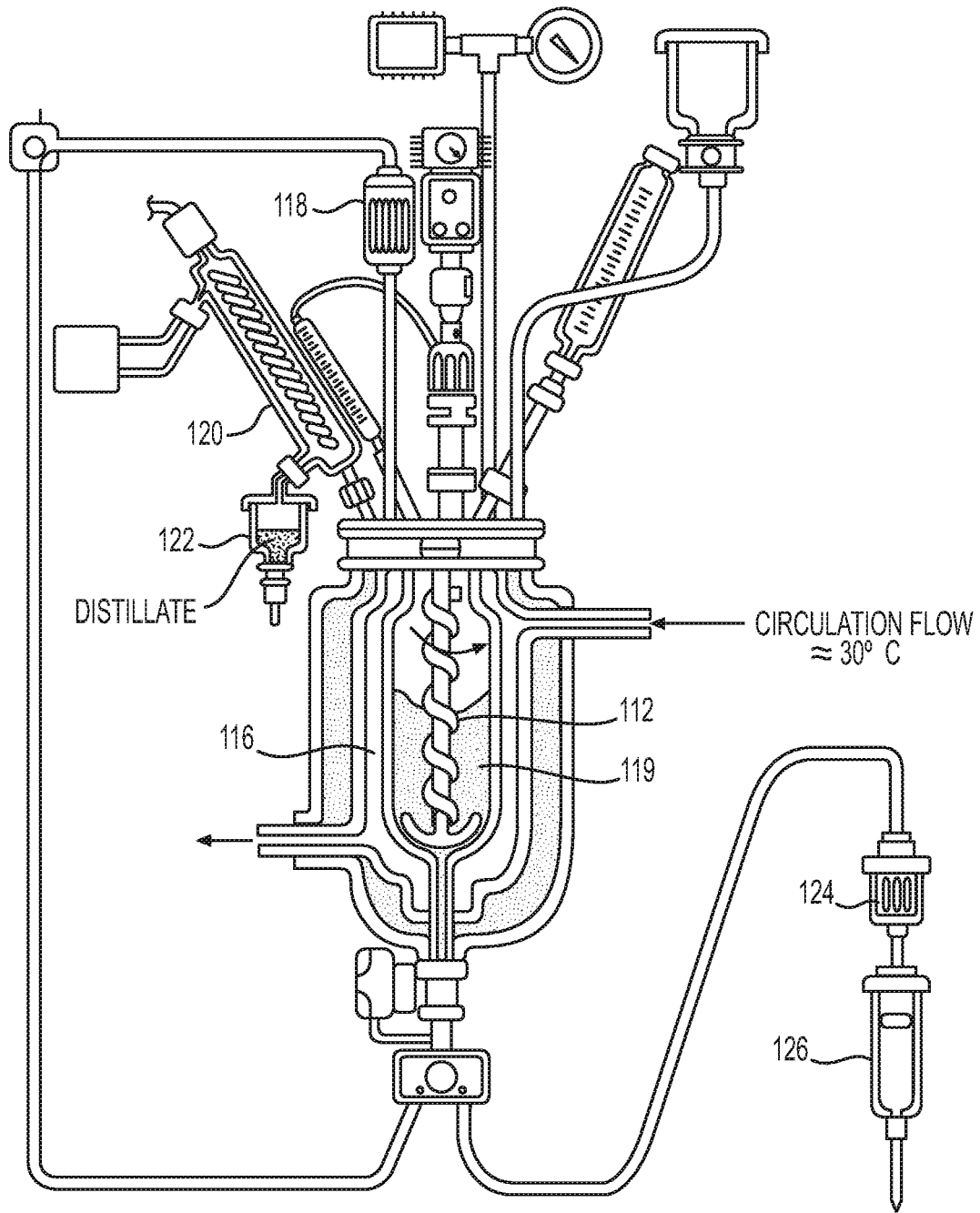
Figure 14:
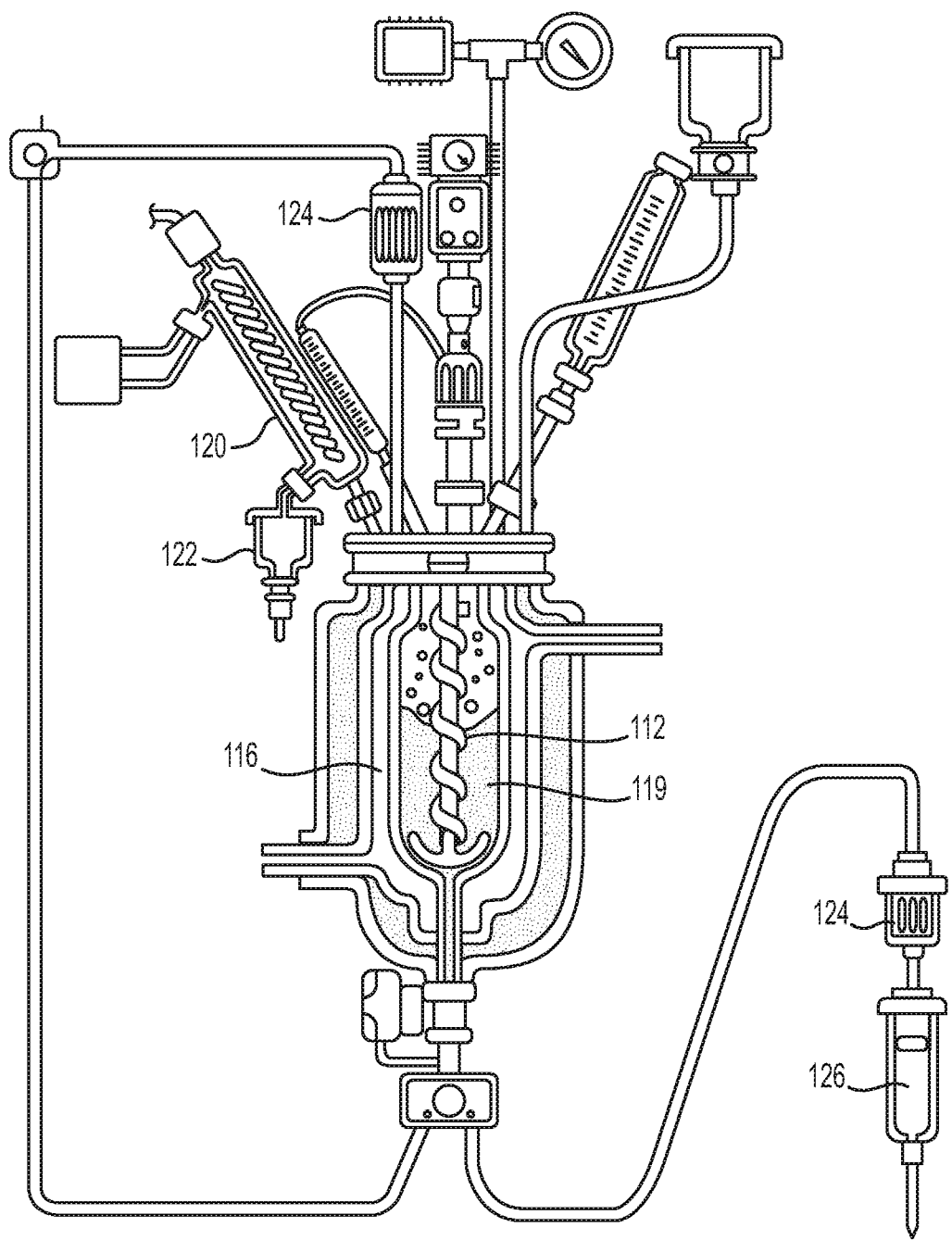
Figure 15:
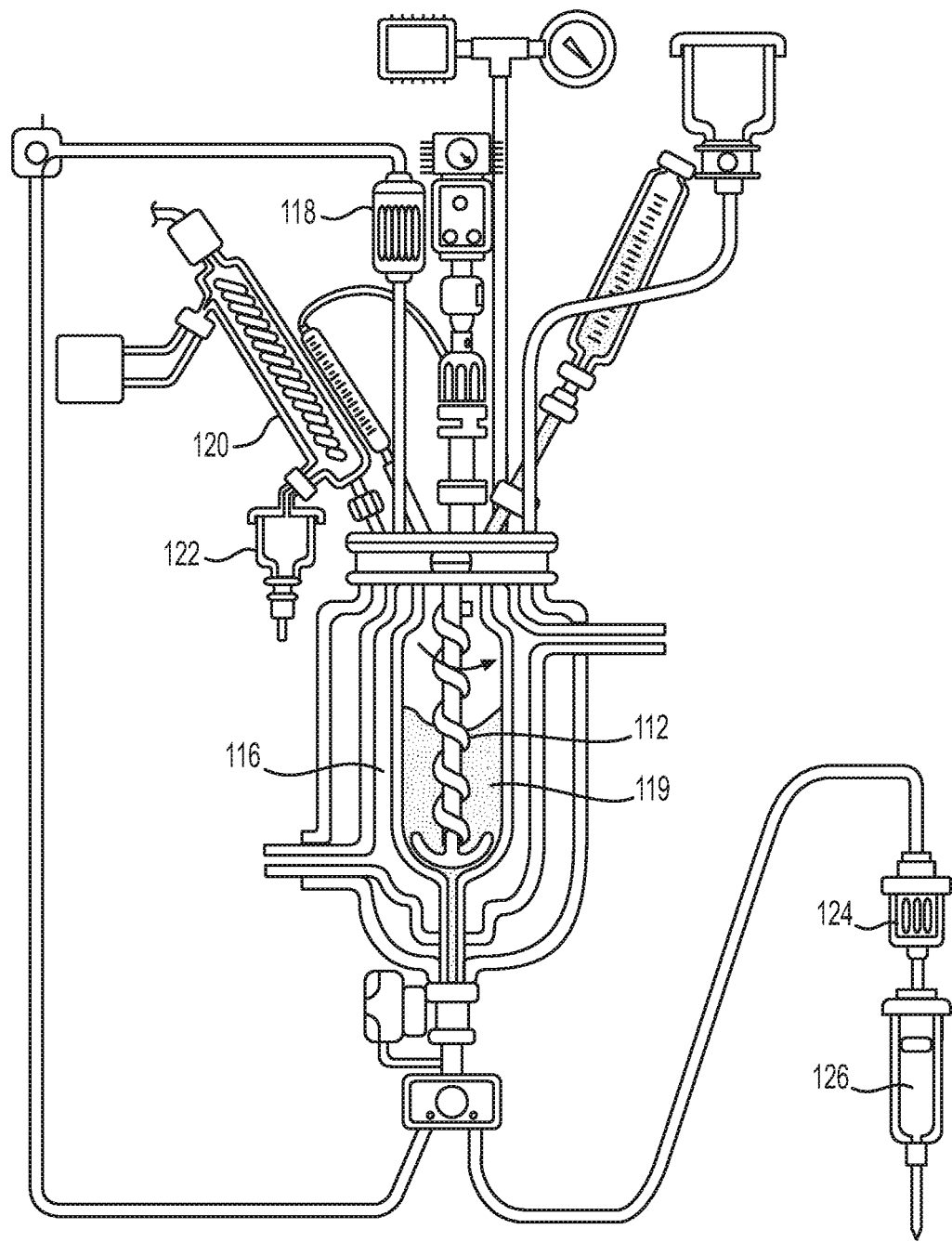
Figure 16:
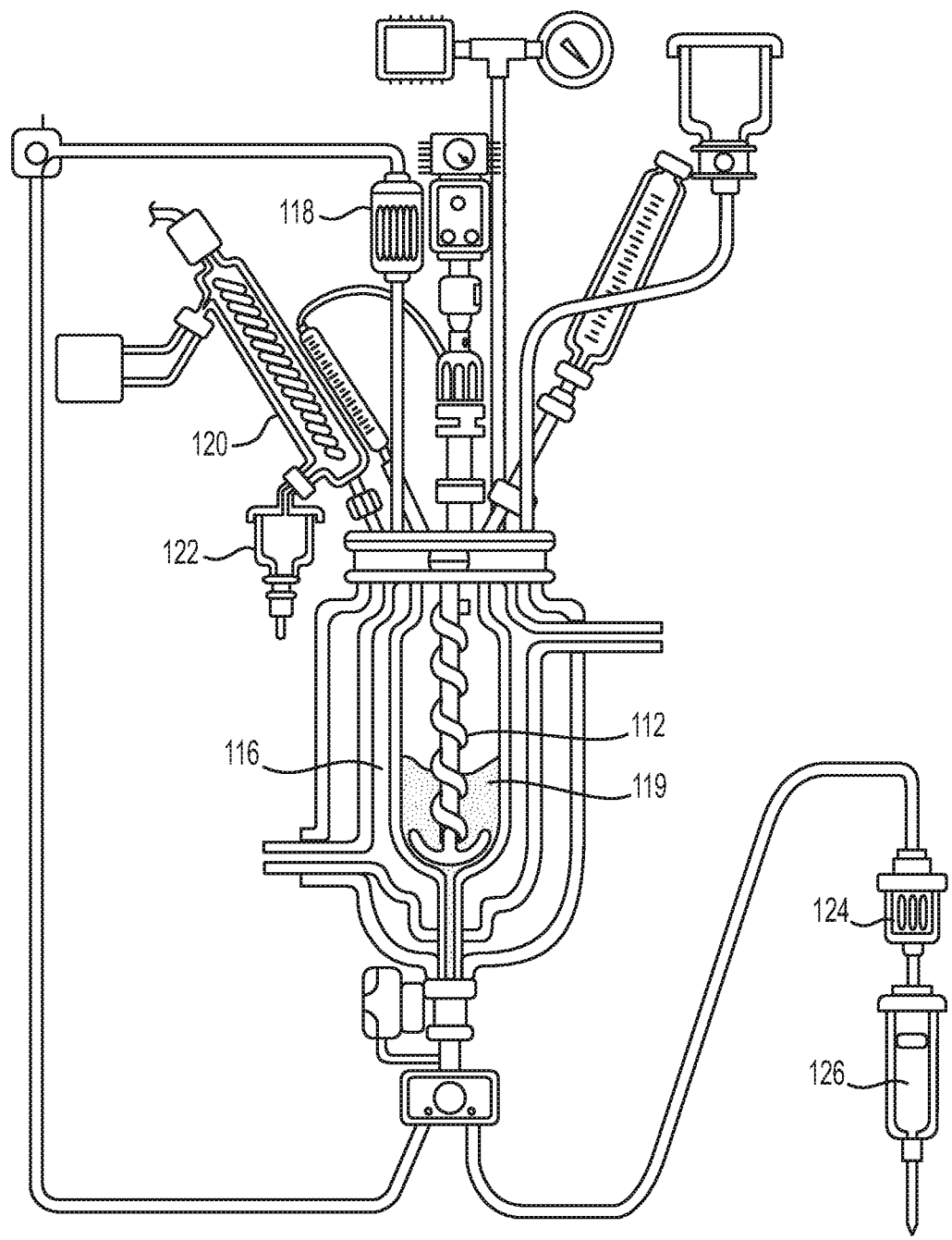
Figure 17:
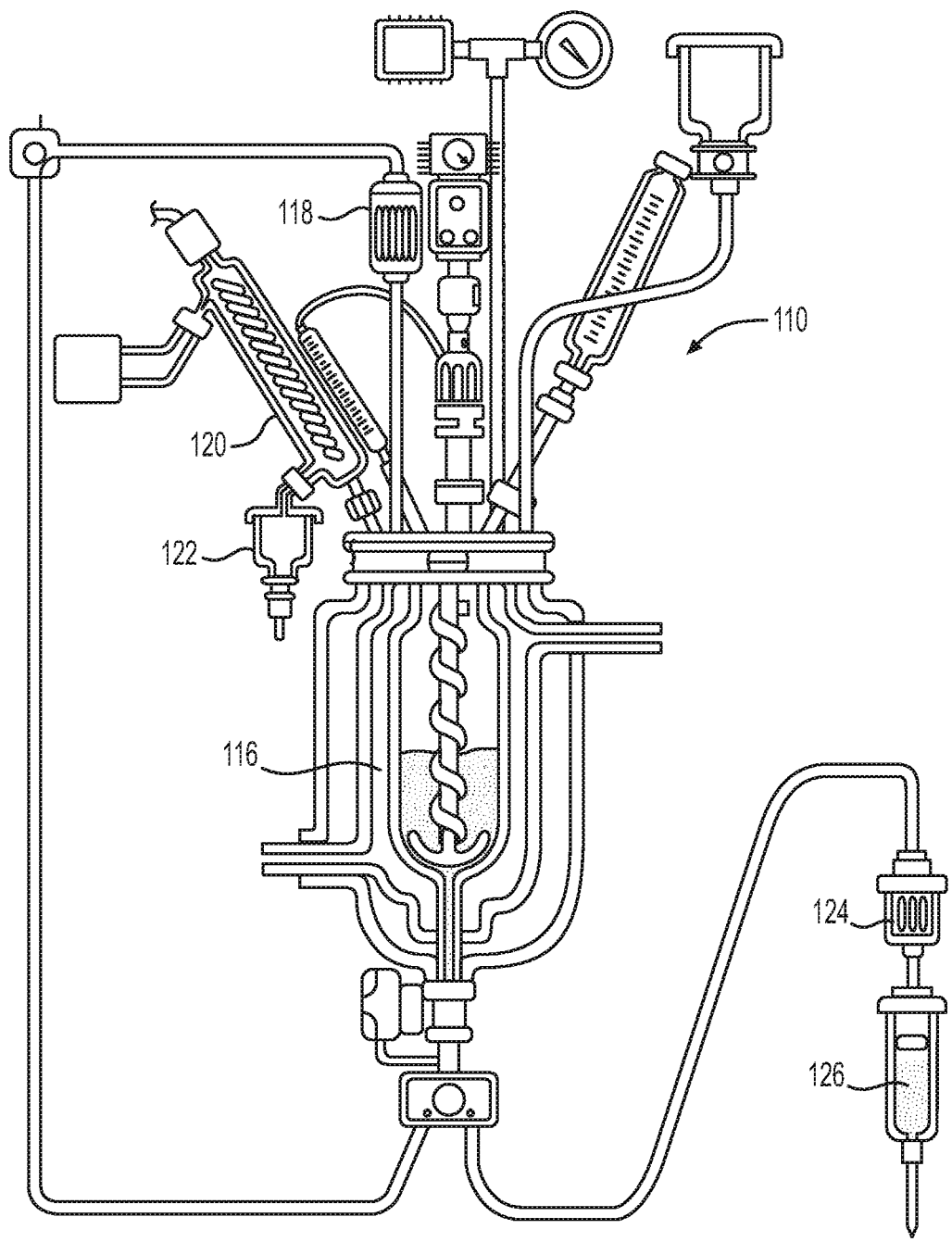
Figure 18:
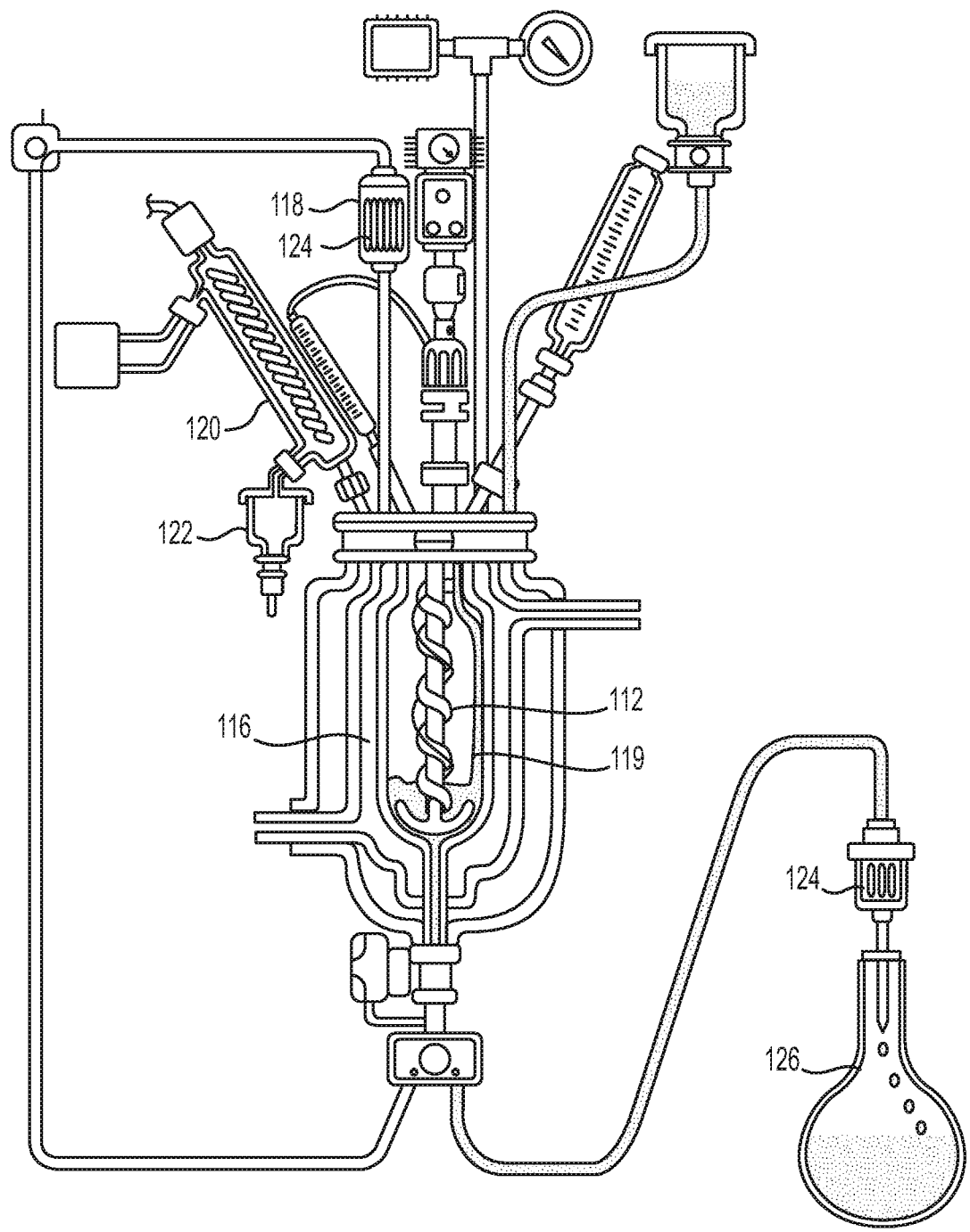

FIG. 11 shows a modified closed loop system with a circulating pump and compressor 101 a cold trap 102 and coalescing filter 103. A back pressure valve 104 Controls the pressure in the processing and drying column.

FIGS. 12-18 show the winterization and filtering 110. Stirrer 112 mixes the material 119. Chiller 116 maintains a temperature of the material. A pump recirculates the material through a filter 118. The alcohol vapors are distilled 120 and collected 122. When the alcohol is out, the recirculation of the material is discontinued and the material passes through a filter 124 and is collected by dripping the material into a flask 126.

Figure 19:
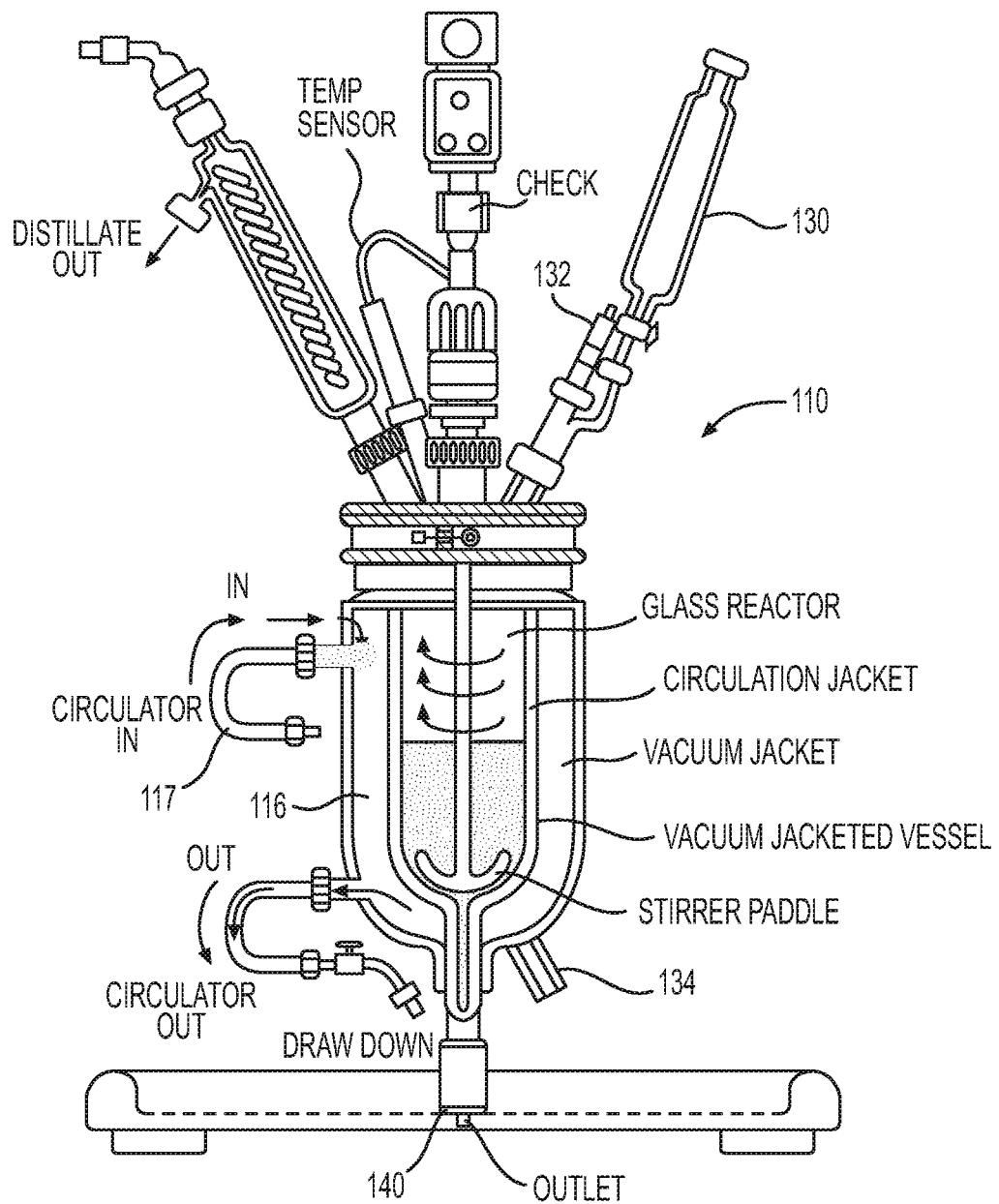
Figure 20:
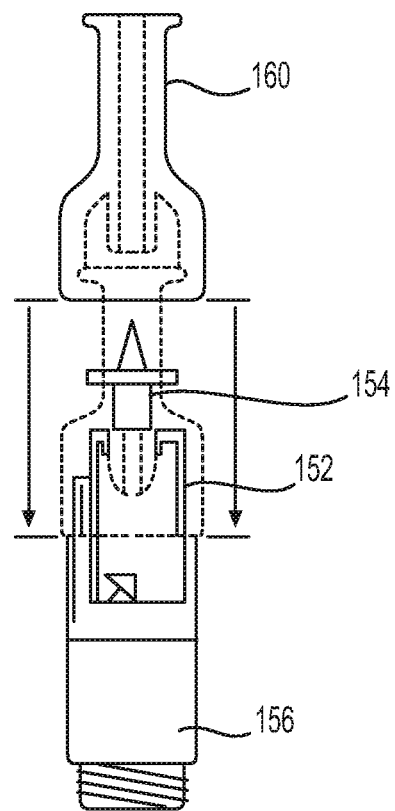
FIG. 20 schematically shows a vapor cartridge.

FIG. 19 is a general schematic showing parts of a distilling system 110. The liquid material is input through a filter 130. Vacuum ports 132 and 134 isolate the system 110. Chiller 116 has circulator connection 117. Outlet 140 is opened to withdraw the liquid after alcohol has been distilled out.

The product is drawn out of the system 110 as a pure oil.

FIGS. 20-24 show packaging, handling and packing of the product.

The oil 150 is placed in a reservoir 152, and a sealing plug 154 is added. A vaporizing heater 156 is contained below the reservoir, and a mouthpiece 160 is connected to the container 162.

Figure 21:
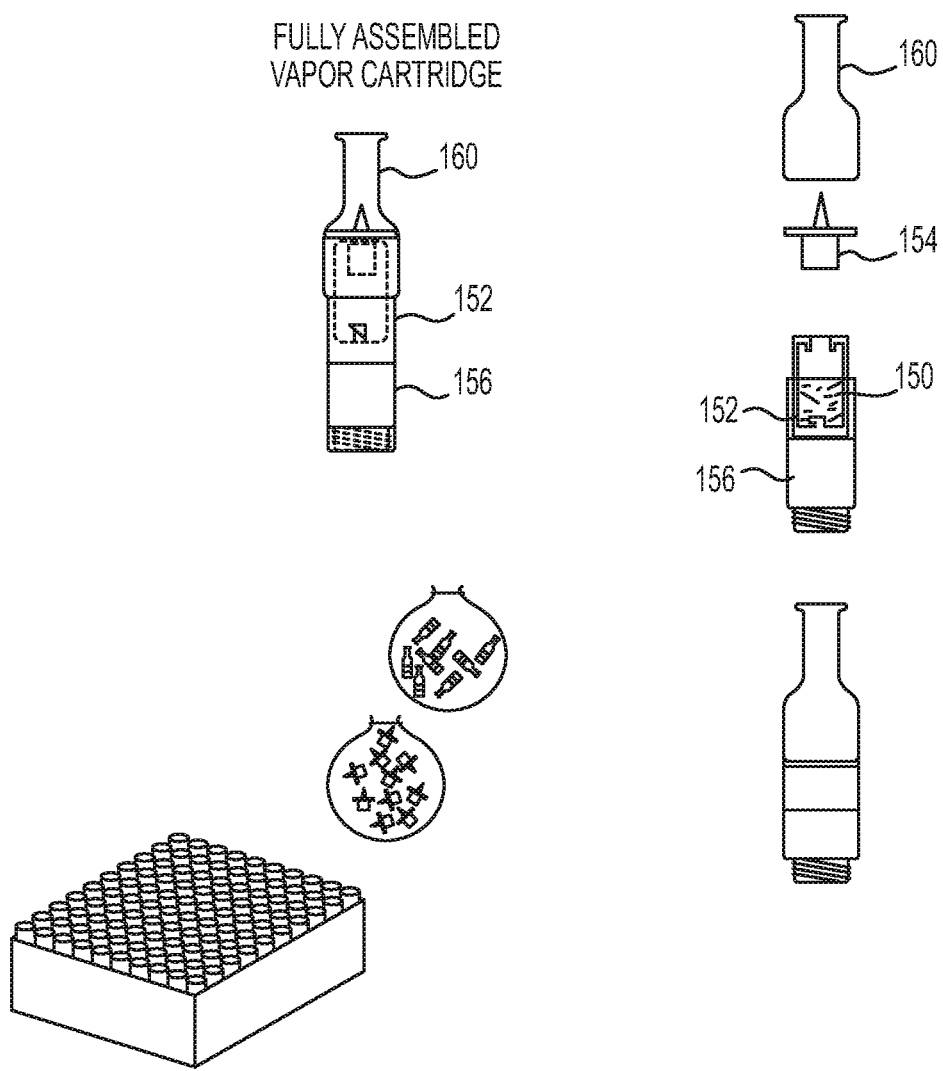
FIG. 21 schematically shows a vapor cartridge assembly.

FIG. 21 shows the assembly and packaging of the container 162.

FIG. 22 shows filling the container through the mouthpiece and plugging and labeling the container with instructions 166.

Figure 23:
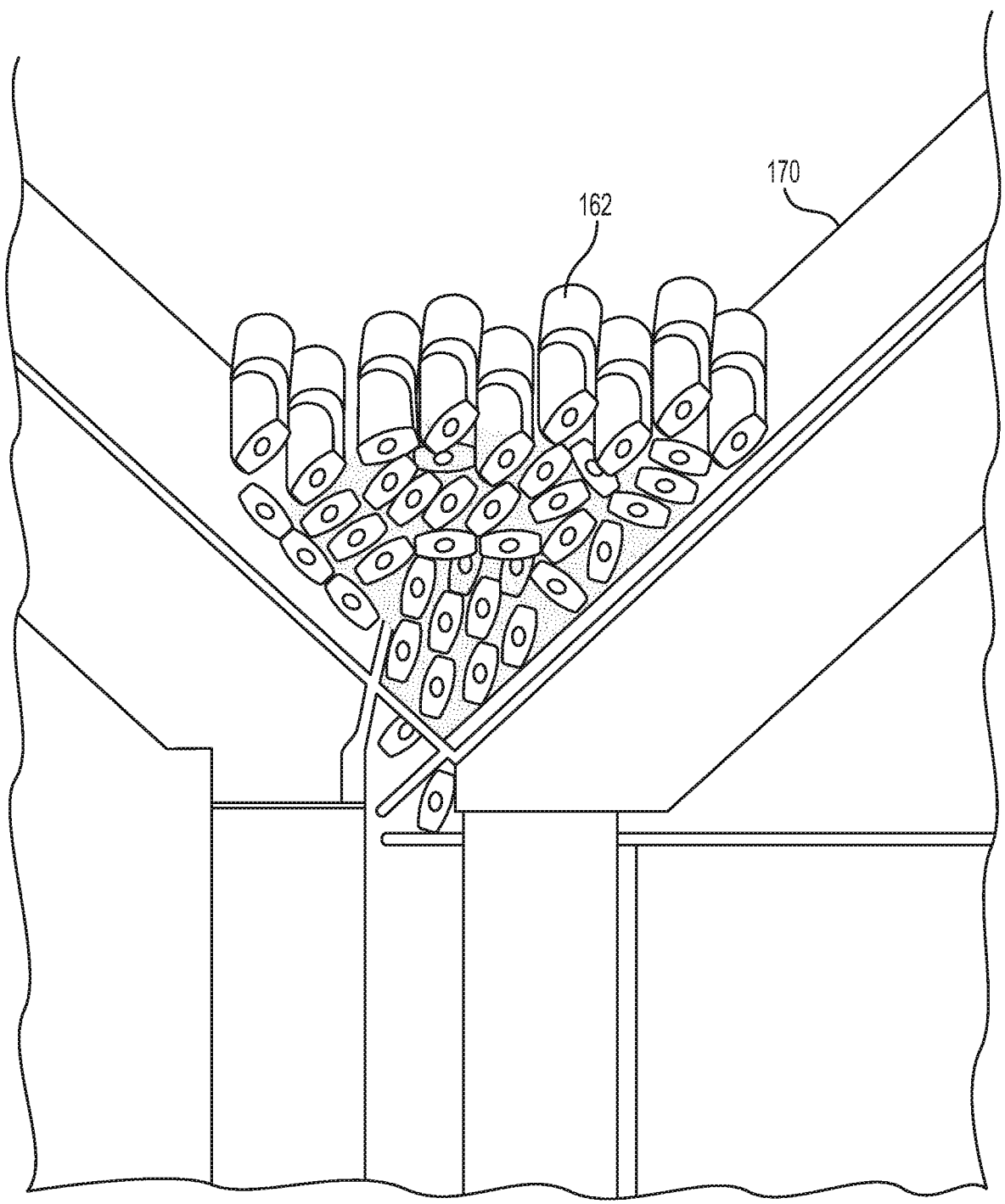
FIG. 23 shows cartridges in a loading hopper.
Figure 24:
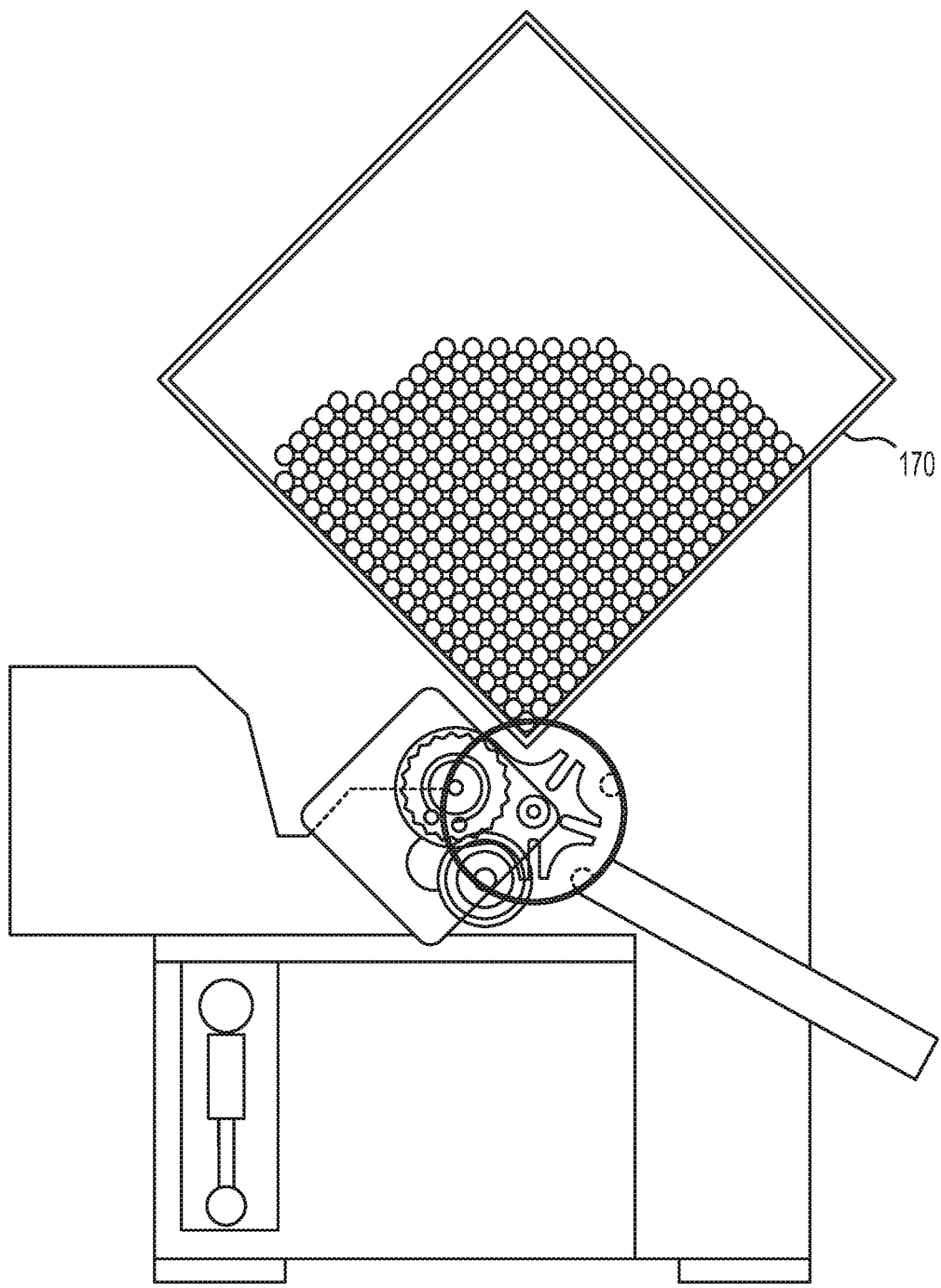
FIG. 24 shows vapor cartridge carton feeding.

FIGS. 23 and 24 show holding and loading the filled containers 162 from a hopper 170 for packaging collections of containers in boxes.

Cryo-Convective Desiccation

In cryo-convective desiccation, "heat" is applied to the substance in a "process column" primarily through convective heating of a circulating gas. Heat is also added by conductive and radiant heating from the column walls, floor, and ceiling. A partial pressure can be created by reducing the orifice size(s) of the inlet flow to the column and increasing the orifice size(s) on the outlet. This can be easily achieved with iris, butterfly, or other type of valves. Iris valves are preferred. A partial pressure can also be created in the process column by a vacuum pump attached to the circulation system, or directly to the column.

The temperature, partial pressure and flow rate are adjusted to achieve optimized water removal rates and dryness. The water removal rate should be moderated so as to not case harden the substrate material thereby inhibiting moisture removal. The colder the desiccation process, the less nutrient loss will occur. A desired balance between nutrient value and drying time can be engineered. Partial pressures can be achieved to sublimate frozen free water. As in freeze drying, heat can be applied to evaporate bound water.

An embodiment configures the process column and circulation system so as to create a fluidized bed in the process column. This configuration offers a clear benefit of the CryoCure System™ over freeze drying in that that it allows a much faster heat transfer of energy to the subject material. This is because the turbulent nature of the fluidized bed randomly, but continually, exposes the subject particles directly to convective, conductive and radiant heat sources. Freeze drying is slow and capital expensive because the heat transfer at partial pressures to material piled in trays is extremely slow even with the use of heated shelves.

Cryo-Grinding

In cryo-grinding, large substance sizes (e.g. whole or shredded leaves) are initially inserted into the column. The flow rate of the circulating gas flowing through the mass of material will tend to lift the mass. Over time the mass will become drier and more brittle. As this occurs, grinding elements within the column are engaged to break up the mass, creating smaller particles. As these particles get dried and the ground particles get smaller still, the grinding process can be accelerated. As the particles get smaller, the flow in the column can be adjusted to act as a fluidized bed. One method uses flexible elements within the process column that rotate, thereby breaking up the material. The flexible members also strike the surface of the filter and conform to it, thereby clearing the filter to prevent clogging. Compound filters can be used to size the grind, and retain the particles in the column. Vibratory means can also be added to keep the filters clear and the gas flowing freely.

Cryo-Bed Vessel

The cryo-bed vessel, aka process column, can be any shape. A columnar bed assists in achieving circular flows from a single or cluster of fluidizing source(s), to reduce "dead spots" in the flow, to lessen temperature gradients, and to allow circular grinding and sieving means.

A columnar bed also condenses the fluidized mass, allowing for more efficient heat and mass transfer from the column wall and the gas flow.

Cryo-Gas Circulation System

There are numerous options for cryo-gas circulation.

A negative pressure, blower circulation approach includes a fan or rotary blower which circulates a gas, such as air, through the material during freezing, sublimation, evaporative desiccation, and/or grinding steps. In one embodiment, a closed loop circulates the gas in the system through a regenerative desiccant dehumidifier (dryer) to continually capture water vapor and vent it out of the system, thereby lowering the humidity in the process chamber and the subject material. A heat exchanger in the system can be added to regulate the temperature of the recirculating gas and, indirectly, the subject material. The heat of the system can thereby be varied to create conditions that freeze, sublimate and/or evaporate the free water in the material. It can also allow the material to be heated for a secondary drying step to remove bound water in the material.

Valves before and after the process column can be used to regulate the process pressure in order to create a partial pressure in the process column to further enhance sublimation. The partial pressure of the system can also be lowered by the use of a vacuum pump.

A compressed air circulation approach—would use a mechanical pump and dryer to flow compressed air through the material. One method uses a closed loop system that recirculates the air through a cold trap to remove the sublimed water from the system. A back pressure valve would be employed to create a negative pressure in the column.

A compressed gas circulation approach uses containers, such as tanks, bottles, dewars or compressors to supply dry pressurized gases to the system and, a vacuum pump to create a negative pressure in the cryo-bed to aid sublimation and exhaust the system. Gaseous nitrogen ($GN_2$) and liquefied nitrogen ($LN_2$) gas are available with low water content and do not need to be dried before use. $LN_2$ or a mixture of $GN_2$ and $LN_2$ are atomized through a nozzle(s). The latent heat of the $LN_2$ or $GN_2/LN_2$ mixture when spray-atomized transfers heat and mass to the contents of the cryo-bed and surrounding structure reducing the temperature of the material and the structure. The gas droplet size, trajectory, velocity and partial pressure of the column is manipulated to create freezing conditions to flash freeze the contents. The gas droplet size, trajectory, velocity, partial pressure and gas temperature of the system can be manipulated to allow conditions to sublimate interstitial water (primary drying) and subsequently to raise the temperature to effect absorbed water sublimation (secondary drying).

As long as the partial pressure of the gas flow is less than the partial pressure of the water in the substrate, the gas flow can be at ambient pressure. Lowering the gas pressure increases the evaporation/sublimation drying rate, but lower pressure also decreases the heat transfer rate. The CryoCure System™ fluidized bed solves this problem by dramatically increasing the heat transfer rate from the vessel walls to the substrate media through conduction, convection and radiation. The increased transfer rate is due to the turbulent flow of the particles in the fluidized bed colliding against the vessel wall and colliding with one another. The system also has the ability to change vapor pressure quickly and uniformly by changing the temperature and pressure of the gas flow.

In the CryoCure System™ the primary objective is preserving nutrient value, reducing water content and providing moderate shelf life extension. In most cases, it is satisfactory to remove all, or a significant portion of, the free water in the substrate by sublimation. Through the variation of temperature and vacuum, it is possible (but not always necessary depending upon the application) to remove all, or a significant portion of the absorbed water content. The use of an inert gas like N2 also serves to suppress loss of nutrient value from oxidation during processing. A compressor and refrigerated and/or desiccant dryer also could be used to create a dry gas flow. In an open loop system, both a pressure pump and vacuum pump can be used. The gas flowing through the system should be pre-dried in order to enable and accelerate the sublimation process. In a closed loop system, both a pressure pump and vacuum pump (or a single dual-function pump) can be used. A circulation loop can be created that recycles the gas through the system and through a cold trap to remove surface and extracted water from the bio-botanical material. The gas flowing through the system should be pre-dried in order to enable and accelerate the sublimation process.

One method uses "dry" (as in extreme low in water content) compressed $GN_2$ and/or $LN_2$ from a supply container, through an inline heat exchanger, temperature controller and nozzle(s), to create a turbulent flow of gas at desired temperatures through the plant material in order to maximize heat transfer between the material and the freezing gas. The temperature of the gas is adjusted to optimize primary (interstitial water) and secondary (absorbed water) sublimation drying. The atomization effect of liquid nitrogen is used as a method of temperature reduction. A negative pressure can be created by achieved by pumping gas out faster than injecting it in, thereby increasing the rate of sublimation.

Freezing System
Pre-Frozen Material

The material to be cured can be pre-frozen by any standard freezing means to reduce processing time. Cryogenic freezing with compressed gases such as $LN_2$, $GN_2$, $LCO_2$, or a mix thereof, are alternate freezing means.

Integrated Freezing

Integrated freezing is better to control and automate the process. Cryogenic freezing with compressed gases is an alternate means to maximize the preservation and nutrient value of the bio-botanical material to be extracted.

Compressed gas when atomized through a nozzle creates a drop in pressure and a subsequent drop in temperature that can flash freeze the material. The turbulent nature of this method enhances sublimation by reducing boundary layer insulation around the material particles.

A negative pressure in the cryo-bed hastens the sublimation process. Negative pressure can be achieved by use of a vacuum pump and by controlling the inlet pressure and volume of the incoming gas versus the vacuum pump rate. Any reduction in pressure below ambient will hasten sublimation, but a vacuum in the 100 mTorr to 300 mTorr range is ideal.

The use of a pressurized liquid nitrogen as the freezing means yields a high quality frozen material, acts as the medium to achieve fluid movement of material in the bed, and increases the heat transfer rate. This allows the freezing to take place with a turbulent flow that will reduce the boundary layer between the freezing medium (e.g. nitrogen or air) and the plant material.

The temperature of the cryo-cure device can be regulated with typical condenser style refrigeration.

The temperature of the device and the plant material can be regulated by engineering the delivery of the compressed gas to achieve both a desired flow rate and a desired gas temperature. This can be achieved by adjusting the pressure drop of the gas across a nozzle and by varying the shape and size of the nozzle orifice.

The temperature of the compressed gas flowing through the material can be further regulated through the use of a heat exchanger in the gas delivery system.

Integrated Grinding

Cryo-grinding can be incorporated within the cryo-bed to perform material size reduction so as to densify the material for later processes. Cryo-grinding is performed after freezing and before sublimation in order the retain nutrients that would be lost during "warm" grinding. Additional cooling may be needed during the grinding process to compensate for heat generated by the grinding process so as to keep the material frozen at all times. Cryo-grinding is preferable to normal grinding because the cryo-embrittled material will fracture more easily, reducing grind time, particle size and mechanical heating, and thereby making it easier to keep the plant material in a frozen state and retain nutrients.

One or more rotating blades can be used to help keep the bed fluidized, as well as to grind the material into smaller granules, or into a powder. A rotating blade at the bottom of the column will cryo-grind the material and keep the bed uniformly fluidized as the material circulates up the column and circulates back down to the bottom. A rotating blade at the top of the column adjacent to a passthrough filter serves to keep the filter clear. The mesh size of the passthrough filter is configured to allow the largest desirable size particle to pass-through and larger than desirable size particles to be retained for further grinding. Additional transverse rotating blades can be used to effect further grinding.

Integrated Sieving

Automatic sieving and exhaust includes a passthrough filter and a trapping filter, a filter clearing device(s), a collection hopper and an exhaust. After the material is ground and sublimated to the desired moisture content, the fluidized bed gas flow and the exhaust vacuum are increased so as to lift the ground material particles against the passthrough filter. Particles smaller than the passthrough filter mesh will travel through it and into a cyclonic filter chamber where the gas is exhausted through a trapping filter, and the retained particles collect in a hopper for later withdrawal. Particles larger than the passthrough filter mesh will not travel past, and the filter clearing device(s) clears the oversized particles and returns them to the process column for further size reduction until they achieve a size suitable to travel through the passthrough filter and collect in the cyclonic filter hopper.

Improved Supercritical Fluid Extraction System

Current Extraction Methods

"Supercritical Fluid Extraction (SFE) is the process of separating one component (the extractant) from another (the matrix) using supercritical fluids as the extracting solvent. Extraction is usually from a solid matrix, but can also be from liquids. SFE can be used as a sample preparation step for analytical purposes, or on a larger scale to either strip unwanted material from a product (e.g. decaffeination) or to collect a desired product (e.g. essential oils). These essential oils can include limonene and other straight solvents. Carbon dioxide ($CO_2$) is the most used supercritical fluid, sometimes modified by co-solvents such as ethanol or methanol. Extraction conditions for Supercritical carbon dioxide are above the critical temperature of 31° C. and critical pressure of 74 bar."—Wikipedia Essential oils that are extracted via the SFE process often include "viscose"; high molecular weight materials which are not easily pumped and which may collect inside the SFE system. In addition to the compounds targeted for extraction, other non-desirable compounds may be extracted using the system with the clear potential for contamination of between run(s). Certain essential oil refining processes utilize the addition of a solvent to create a dilute solution that then undergoes a winterization process and filtering process to separate the lighter oils from the heavier fats and waxes.

Improved Extraction Method

The improved SFE system includes piping, valving, pumping and controls that allow the system to be flushed with a solvent between production runs, or between segments of a production run. The solvent flush can be pumped into the supercritical fluid circulation system either before, or after, the extraction vessel. Injecting the solvent before the extraction vessel provides a more thorough flush and acts as a co-solvent to remove additional oils and waxes. Injecting afterward the extraction vessel bypasses the compacted material in the vessel and allows flushing at a lower pressure and thereby a less expensive pump.

The solvent used to flush the system is the same solvent that is used in the subsequent winterization process, thereby combining both flushing and solvent addition in one step. This is advantageous because using a flushing solvent like Ethanol is expensive and using the same solvent for flushing and winterization saves time and reduces solvent usage.

Improved Method of Extraction & Fractionation

An improved method of extraction and fractionation described here includes components, which can be used individually or in combination. There are:
SFE Mapping
SFE Programmed Selective Fractionation
Step & Flush Separation

SFE Mapping

In this first step, a series of extractions and test are performed on a subject material over a range of pressures, temperatures, flow and time conditions to create a map of process variables and resultant extracts. The process begins with conditions that create a subcritical fluid and increase at a continuing rate, or at discrete intervals, to a desired upper test set-point limit for each of the variables. As subcritical and supercritical fluid temperatures and pressures are increased, so is the solvating power of the $CO_2$. Samples of the resultant extract from subject material are taken at correlating intervals, and the samples are weighed and analyzed using spectroscopy to determine what analytes are present and in what amounts. This information will determine the analyte's solvability within a process window.

The data from the tests are plotted to create a process capability map that shows the amount of each analyte extracted at each sample point. Maps are drawn for each analyte showing a topography of conditions which yield extract from the analyte and in what amounts.

A database of process maps for subject materials can be references for a subject material to create a reference process map. As the data base builds, the reference map will become more accurate in optimizing targeted analyte yields.

Programmed Selective Fractionation

Because the solvability of different compounds within the subject material will vary, it allows the use of a process of sequential and selective fractionation. The program begins with conditions to extract high solvability compounds first and proceeds to conditions that extract the low solvability compounds. If done in reverse, all compounds will be extracted, thereby defeating the purpose of the sequence.

Once the programming of the process is completed the subject material can then be extracted using a sequential set of conditions that maximize the yield of targeted products. The extract from each set of conditions can be collected separately by either changing the collection container or directing the extract into a product-specific container.

This process will create extract fractionation from the subject material with a higher concentration of the target compound than using pressure drop fractionation alone.

For production extraction, processes can be set using existing reference maps and process programs for similar materials being extracted. Additional testing tests can be added that use pattern recognition algorithms to adjust for variations in materials.

As the database of mapping grows, historic reference maps can be used to create an abbreviated program that is supplemented with live testing during extraction to fine tune the result without having to complete a complete mapping sequence on each run.

One method of analysis is to perform in-line spectroscopy to gather the data directly from the process rather than take samples and test off-line.

This extraction process mapping and subsequent programmed fractionation can be done in separate steps or can be performed sequentially within a single combined analysis and extraction process.

Step & Flush Compound Isolation

After each compound has been substantially extracted within its optimal process window a solvent such as ethanol is injected into the system to flush the system to dissolve and remove residual extracts that clings to piping walls and valves.

The solvent can be injected before or after the extraction vessel so as to flush the SFE system. Injecting before the extraction vessels will provide a more extensive cleaning but will this will also act as a co-solvent and this could affect the contents of the fraction by removing integrated compounds. Injecting after the extraction vessel will flush the system without adding un-targeted, co-solvent, extracted compounds.

One method runs experiments to create an extraction profile on the subject material, varying pressure, temperature, flow and time across subcritical and supercritical fluid conditions while simultaneously performing in-line spectroscopy. From this data a topographical profile can be created to determine which extraction profile best extracts specific compounds.

Based upon this extraction profile, a stepped extraction profile sequence can be initiated so as to extract a particular compound and collect it into a collection vessel. When a particular compound has been fully extracted, it can then be discharged from the extraction system into a dedicated container. A distribution valve can be used so that an automated sequence can occur to allow stepped, process-defined fractionation into multiple containers.

Combining inline spectroscopy, extraction profiling, stepped process fractionation, step and flush isolation, and directed discharge allows a highly-automated compound concentration.

Step and flush fractionation allows fractionation using a single separation vessel, rather than requiring multiple separating vessels.

Bio-Botanical Oil Refinery

The Bio-botanical Oil Refinery is an apparatus and method for automating and integrating the multiple steps of: winterization, filtering, distillation, decarboxylation, dilution and polishing of extracted bio-botanical essential oils into a unified manufacturing process.

1. Infeed

During the infeed step, an alcohol and extract solution is fed into a pre-chilled vessel, in one embodiment a vacuum jacketed vessel (VJV), by gravity, or pump. The solution also could be pre-chilled to reduce processing time. Additionally, a pre-winterized and filtered solution could be used to reduce processing time.

2. Winterization & Filtering

At the start of the winterization and filtration step, the process vessel is chilled by the thermo-regulator and circulator according to a programmed temperature profile. A stirrer starts the mixing mode to aid in chilling and maintaining temperature uniformity. As the solution transitions through the chill temperature profile, fats, waxes and certain other undesired substances will agglomerate. The agglomeration of these different substances will occur at different temperatures.

Throughout the process, the outfeed pump continuously, or semi-continuously, circulates the solution through a filter array and back to the vacuum jacketed vessel (VJV). The directing manifold can direct the solution to different filters in the array to allow fractionation of the agglomerate.

A sensor can be added to measure the clarity of the circulating solution as it circulates. The system can be programmed to circulate and filter for a specific period of time, or to filter to a set-point on the clarity sensor.

Upon completion of winterization and filtration, the process vessel circulation pump stops, and the outfeed valve switches to OFF.

3. Distillation

At the start of the distillation step, the temperature regulation and circulation system is switched from chilling to heating and a vacuum is drawn on the process vessel. The solution is heated to ~30° C. Chilled water begins circulating in the condenser.

The stirring system changes to distillation mode to aid evaporation by channeling the solution to the coat the inside wall of the VJV creating a film and increasing the evaporating surface area. The alcohol evaporates and the condenser collects it into a collection flash. Distillation continues until the alcohol has been removed and what remains is the raw filtered extract.

4. De-Carboxylation

To begin de-carboxylation, the stirrer switches to de-carboxylation mode while slowly stirring the extract. The thermal regulation and circulation system is switched from chilling to heating. A vacuum is drawn on the VJV and maintained at a setting of approximately 0.1 atmospheres.

The temperature of the extract is raised to its de-carboxylation temperature (~125° C.). Bubbles start to form from the de-carboxylation process. As the bubbles form the vacuum level will drop and the vacuum system compensates by drawing more vacuum to maintain the vacuum level. One method of adjusting the vacuum level is by burping it with bursts of vacuum so as to avoid foaming the material.

De-carboxylation continues for a specific period of time at the set point temperature and until the outgassing stops. The vacuum is turned off.

5. Optional Dilution

A diluent is injected into the process vessel to achieve a desired viscosity. Typical diluents include; poly ethylene glycol (PEG), propylene glycol (PG), vegetable glycerine (VG), terpenes, or a mixture thereof.

Throughout this step the stirrer mixes the diluent into de-carboxylated extract.

6. Optional Polishing

In an optional polishing step, the stirrer mixes the solution to achieve uniformity. Coincidentally, the temperature of the extract solution is reduced to a safe handling temperature.

The outfeed pump then starts. The outside valve opens, and a diverter valve directs the extract solution through the polishing filter.

7. Discharge

In the discharge step, the extract solution is directed from the polishing filter into a collection vessel. A slight positive pressure can be applied to aid in fully discharging the extract solution. Upon completion, the extract solution collection container is removed.

8. Rinse

A rinse cycle can be added to inject alcohol into the process vessel. The resultant solution is stirred, and then flushed into a flask.

The collected rinse may then be distilled offline to reclaim any desired residuals.

Filling & Labeling

Background on Cartridge Delivery Systems

Vape cartridges (aka cartomizers or clearomizers) are containers with a vaporizing heater, screw thread or magnetic mount, reservoir for holding oils, a sealing plug and a mouthpiece. The cartridge is typically attached to a battery. When initiated by a low pressure switch, timer or ON button, the heater vaporizes the oil. Vapor is then drawn through a passage in the cartridge body, then through the mouthpiece, and then into the user's mouth, throat and lungs.

These cartridges are typically made in China and shipped to e-cigarette and cannabis businesses around the world where they are filled with so-called "e-juice", or cannabis oil. E-juice is typically mixture of a vaporizing oil (such as poly ethylene glycol (PEG), propylene glycol (PG), vegetable glycerine (VG), terpenes, or a mixture thereof) and nicotine, nutraceuticals and/or flavorings. Businesses typically make, or blend oils, fill, assemble and pack the cartridges before shipping them into distribution.

Vaporizers cartridges are also known as cartomizers. Cartomizer refers to the fact that the cartridges have built in heating coil to vaporize the oil. The cartridges are shipped fully assembled (without oil), or fully assembled except for the plug and mouthpiece (also without oil). The cartridges are typically individually packaged or packed in some form of foam tray in a chipboard carton and then placed in a master corrugated cardboard carton. The cartridges screw onto a battery for power and vape control.

The body of cartridge has one or more heaters, a heating chamber, usually a fiber glass or porous ceramic wick, a reservoir for the oil, an air passageway, a removable plug to contain the oil and a mouthpiece, aka "tip".

The finished cartridge is typically packaged in a clear plastic tube with end caps. Sometimes the cartridges are shipped in the tubes and sometimes they are shipped separately. The cartridges are typically filled manually or with filling automation. If the cartridge comes fully pre-assembled, the tip and plug must be first removed. The cartridge is then filled, re-plugged and re-tipped. The tip of the cartridge is often printed with a small color-coded logo to denote the contents of the cartridge.

The finished cartridge is then typically inserted into the tubes and occasionally labeled then either put into a sealed "medicine bottle" or simply inserted into a printed cardboard holder.

Cost Inefficiencies in Current Delivery Practices

The filling of the cartridges is done either manually with a syringe or automatically with a filling machine. After filling, the cartridge is manually sealed with a silicone plug and a mouthpiece is attached, before being packed for sale to consumers. The added labor cost is significant. In all current known cases the cartridges have to be removed from their current foam package before being placed in the automation wasting more valuable labor time. Manual filling with a syringe is inaccurate and in order to prevent underfilling, cartridges are typically overfilled, adding to additional cost inefficiency.

Because the market is highly fragmented, there are a large number of small users. The small users find it difficult justify the automation investment. As a result, there is a great deal of lost profit margin due to the excess labor involved in delivering the finished product to the user. Most current product designs allow the mouthpiece and plug to be easily removed and replaced without leaving evidence of tampering. There is little or no information on the cartridge to designate what type of oil is inside nor is there any lot code information.

As a result, there is little ability to authenticate, track and trace the cartridge. Users with a variety of cartridges have no way to distinguish one from another. This can lead to a poor user experience, or worse, incorrect dosing or incorrect medication.

Improved Delivery System

The invention is a system that reduces transportation costs, reduces labor costs, simplifies the filling and assemble process, reduces the cost of over-filling, provides identifying graphics and text for users, and provides authentication, tracking and tracing.

System Elements

The system includes the following elements:
- A master database and satellite databases that collects authenticate, track & trace information on the manufacturing supply chain.
- An oil supply container with a code that identifies the contents of the container.
- Cartridges that are fully assembled, consisting of a cartridge body, plug and mouthpiece,
- An attached optional tamper evident wraparound label, with optional branding graphics and contents information
- A unique cartridge-identifying means attached to the label or the cartridge, such as an RFID tag or bar code.
- A means for reading the identifying code on the oil supply container.
- A device that reads the identifying code on empty cartridges, references that against a data base and matches it to an approved list, authorizes the device to fill the cartridge, records the identifying information on the cartridges filled from the supply container and adds the information to the database. Optionally the system can print the contents directly onto the cartridge
- A device that fills the cartridge through a hole in the attached mouthpiece by use of a custom syringe. In addition to the value of simplifying the filling process by eliminating the need to remove and restore the mouthpiece, this feature allows for permanent attachment of the mouthpiece. Permanent attachment adds a tamper-resistant quality to the product and also limits the ability of the end user to refill using current methods.
- A device that rotates and prints directly on the cartridge utilizing the syringe needle as an axis of rotation. Optionally, the printing can be done on a pre-applied label. This label can be blank or be partially pre-printed; logo, standard information, etc.
- A cartridge with a radio frequency identification (RFID) tag, bluetooth or WWI like communicator built into the cartridge, or into its matched battery's electrical circuit such that the circuit will not turn on unless it receives authorization from a proximate approved user authentication device.

A cartridge and battery with built-in approved user authentication device such as a "fingerprint" reader. Such "fingerprint" reader could be a sensing device that reads actual fingerprints or reads a thermal pattern from the approved holders grip on the device.

Product

Empty cartridges, hereafter called V-0's, are sealed with a plug, membrane or dispensable sealant, and assembled with mouthpieces at the origin factory. The plug, membrane or dispensable sealant is made from a rubber-like material that allows it to function as a self-resealing septum. A syringe-like device inserts a needle through the opening in the mouthpiece, penetrates the septum and fills the cartridge without having to remove the mouthpiece or plug. It also allows pre-labeling of the cartridge.

Packaging

The V-0's can be dense packed in shipping trays or magazines.

The trays or magazines are designed to protect the cartridges from damage and contamination during shipping. They are also designed to be loaded directly into the HES filling machine, eliminating re-handling labor costs.

Filler Operation Sequence

The process for filling is as follows:

A tray or magazine of assembled cartridges is positioned in the machine, or hand loaded into a hopper or infeed device.

A mechanical device with one or more precision filling syringes and needle(s) moves to a position adjacent to the cartridge(s) and enters through a hole in the mouthpiece of the assembled cartridge. It makes contact with the cartridge septum, pierces the septum, dispenses the vape oil inside the cartridge and then withdraws.

The design of the septum is such that the assembled mouthpiece holds the septum preventing it from being pulled out of position during needle withdrawal.

A stripper feature can be added to the needle assembly to hold the cartridge in place during needle withdrawal.

A chuck can be added to the needle assembly to center the cartridge for filling.

The Septum can be the current silicone plug which includes a cone "handle", a modified silicone plug with a flat or recessed surface to aid needle alignment, a disc-shaped self-re-sealing membrane adhered to the needle opening surface, or a dispensed sealant can be used to seal the cartridge and create the septum.

The end result is a highly efficient system with low capital costs that minimizes shipping, labor, and overfill costs as well as providing valuable information to the user and provides authenticate track and trace means.

Labeling

Cartridges should be able to provide medical, contents and other detailed information as well as branding marks and graphics. Cartridges should be sealed and tamper evident to prevent reuse, to reduce the risk of misuse and the related liability.

This invention includes and apparatus and methodology to print a label with graphics, medical and/or and contents information and apply a label on the barrel's outer diameter, thereby sealing the mouthpiece to the cartridge body. This will both create a tamper evident seal as well as provide needed surface area for graphics and consumer information. The label could be a simple strip label running vertically on the cartridge, a label that wraps around the barrel, or even a label that is attached to the cartridge but has an extended portion that wraps additionally around the cartridge body. The extended portion could have a perforation to allow easy removal, or it could have a reel-able adhesive to allow the extended portion to be unwrapped and rewrapped. The extended portion could also be used as a consumer "coupon".

The labels can be printed directly on the cartridge, or pre-printed, partially pre-printed or printed on demand and applied to the cartridge. The label can be clear, or have a clear, or cut, window to allow viewing of the contents. The label has a unique identifying code such as a bar code or RFID tag.

Cartridges are removed from a tray or fed from a magazine, moved to a labeling position and labeled by direct printing or by a simple tamp-on application of a partial label, or rotated while a wraparound label is printed or applied. The labels can be pre-printed to allow high quality graphics and then printed again, before, or after application to provide serialization and other information.

The labeler can have printing and serialization capability to provide authenticate, track and trace features.

Cartridge Design for Labeling

Typical cartridges 100 have a removable mouthpiece 101, which allows access to the plug 103 and cartridge 105 for re-filling. While this is useful, for many applications, especially for medical marijuana, the cartridge should be non-fillable and should be tamper evident. In addition, the cartridges are not designed to provide the ability to easily add customized and high quality graphics suitable for marketing, nor are they designed to be easily marked with content information for medical, or consumer use. The mouthpiece can have an orientation feature to allow easy alignment of the mouthpiece with the cartridge.

This invention provides product 110 where a wraparound label 120 is applied to the cartridge such that it overlaps the mouthpiece 111, reservoir 113 and optionally the metal mount 105. This wrap around label 120 can also have an extension 121 to allow additional content information such as medical and tracking information Clear windows 123 allow users to see the fill level of the cartridge. The design of the typical cartridge is such that there is a significant volume of above the visible portion of the reservoir so that when the cartridge is placed on its side, or inverted, a significant amount of the contents hides in the hidden volume so that when the cartridge is righted, the reservoir provides false information until eventually the oil slowly flows back into the reservoir.

This invention produces product where the interior of the tank is made so the contents are fully visible and the interior of the reservoir has a nearly flat roof, corner radiuses and an interior finish that aids in the reflow of the oil to provide more accurate visual level indication. Because the cartridge will wick some oil into the vape chamber after filling, any amount of hidden space should not be more than what is wicked into the vape chamber.

Figure 26:
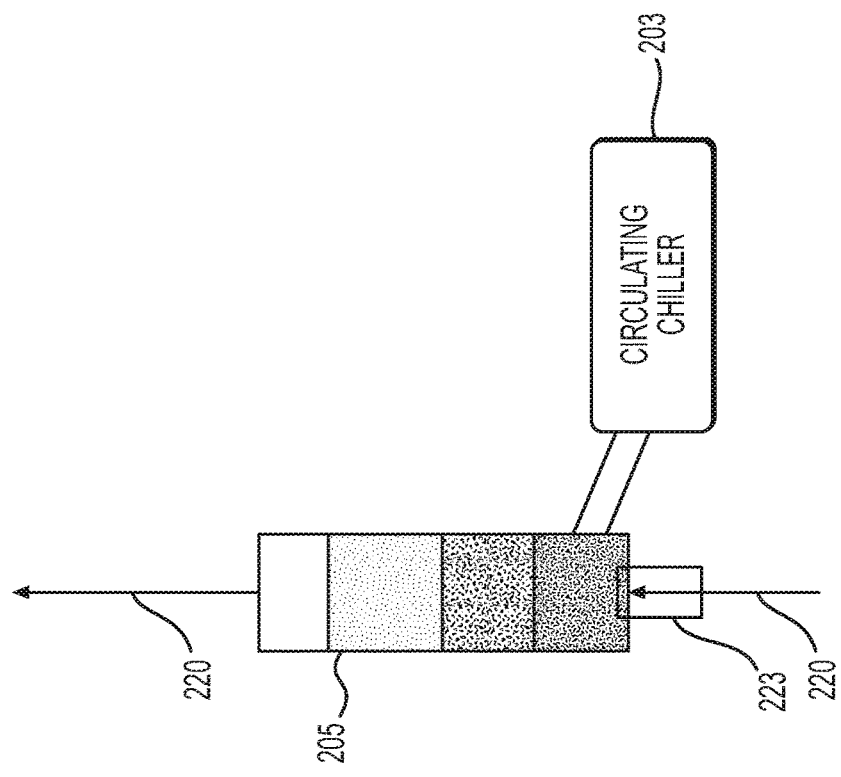
FIG. 26 shows a multistage molecular sieve.

The CryoCure Bio-botanical Drying System 200 shown in FIG. 26 ("CryoCure System") is a system for removing water and other volatiles from bio-botanical materials without exposing the material to environmental conditions, such as heat, that cause the loss of nutrient value through evaporation, oxidation, or chemical changes.

The system includes the following components:

1. Cryo Vessel—is a container that holds bio-botanical material 221 for desiccation. It is operated at sub-atmospheric pressures and near freezing and/or sub-freezing temperatures. It has a gas circulation system and an inert gas supply 230.
   a. Freezing and near freezing temperatures retain volatile and easily oxidized nutrients and retard naturally occurring chemical changes.
   b. Negative pressures increase sublimation of water vapor and volatile components.
   c. Gas circulation transports the water vapor and volatiles away from the chamber for subsequent cryo trapping & adsorption; and allows dry gases to return within the closed loop system.
2. Cryo Chamber/Cryo Trap 202—is a negative pressure chamber that is chilled to sub-freezing temperatures.
   a. Sublimated water vapor condenses and freezes on the chamber wall and/or cooling coils, trapping and removing water from circulation. Some volatiles are also trapped with the condensing water vapor.
   b. The deeper the vacuum the easier it is to achieve lower cryogenic conditions in the chamber.
3. Recirculating chiller(s) 203 (liquid nitrogen dewar, or other temperature reducing means) is used to remove heat from the Cryo Vessel 201, Cryo Chamber/Trap 202 and circulation piping 223 so as to decrease and control the temperatures within the system.
4. A Pump 204 and/or Blower is used to create negative pressure in the Cryo Vessel and Cryo Trapping Chamber 202; high pressure in the return loop and optional adsorption column; and circulate the gases within the system.
   a. The circulating gases 220 aid in sublimation by conveying the water vapor to the Cryo Trap 202 thereby decreasing the humidity in the Cryo Vessel 201. The lower the relative humidity in the Cryo Vessel the faster: water vapor sublimes, is carried away, trapped and removed from circulation. As water is trapped the relative humidity of the circulating gases drops and further sublimation is enhanced.
   b. The pump adds heat to the circulating gases.
5. Desiccant/Adsorption Column 205 as shown in FIG. 7 is a closed container with one or more stages of desiccating and/or adsorption materials.
   a. Adsorbent materials have affinity for different gases to varying degrees based upon concentrations, temperature and molecular sizes. e.g.
      i. Silica gels re highly effective at high but poor at low $H_2O$ concentrations.
      ii. Molecular sieves are excellent at low but poor at high levels of $H_2O$
      iii. Molecular sieves are excellent at separation by molecular size.
      iv. A multi-stage column can be built with a stack of different desiccants that work in concert to trap $H_2O$ vapor and other volatiles to remove them. If the stack is arranged from smallest molecular sieve size to larger sieve size then sequential fractionation will occur. Each sieve capacity can be engineered so as to capture all of a specific range of molecules so that separation of molecules by molecular size can be achieved.

Figure 27:
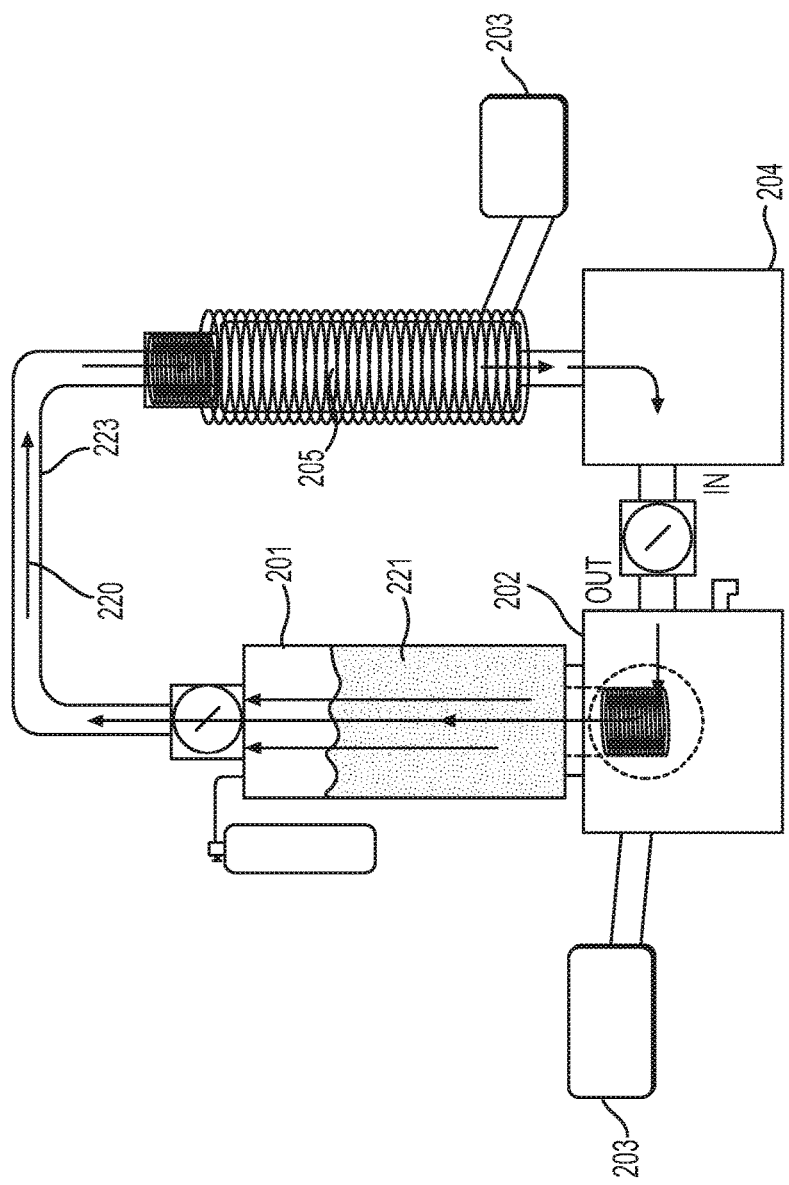
FIG. 27 schematically shows an up flow CryoCure system

One embodiment is the Up Flow CryoCure System 200 shown in FIG. 27. Bio-botanical matter 221 is placed into the CryoCure Vessel 201. A recirculating chiller 203 reduces the temperature in the CryoVessel causing the bio-botanical matter to freeze. A pump 204 draws a vacuum on the vessel creating a vacuum within the Vessel 204 and CryoChamber 202 and causes the water in the bio-botanical matter to sublimate. A piping system 223 transports the water vapor and volatile gases from the CryoVessel through a pump, positive pressure chamber, throttle valve and back to the CryoChamber. The closed-loop arrangement of CryoChamber, CryoVessel, piping, pump, positive pressure column and throttle valve 231 serves to create positive and negative pressures as well as transport the sublimated water vapor away from the bio-botanical matter and trapping it in the CryoChamber and/or in adsorption material(s) within the Positive Pressure Column. Trapping and adsorbing the water vapor serves to reduce the chamber humidity and enhance the sublimation of water from the bio-botanical matter. Up flow 231 of water vapor and gases serves to loosen the bio-botanical matter within the CryoVessel 201 and helps prevent compaction. If the upflow is increased it will also create a fluidized bed mixing the material 221 and help to prevent stratification of the matter. A mixing blade can be added to assist in mixing and "fluffing the material to enhance the flow of gases and sublimation of water from the bio-botanical matter. The mixing blade can also be used to cryo-grind the frozen and thereby embrittled matter.

Freezing and thaw cycles can be used to rupture cell walls to enhance sublimation and extraction of essential oils in subsequent processes.

Figure 28:
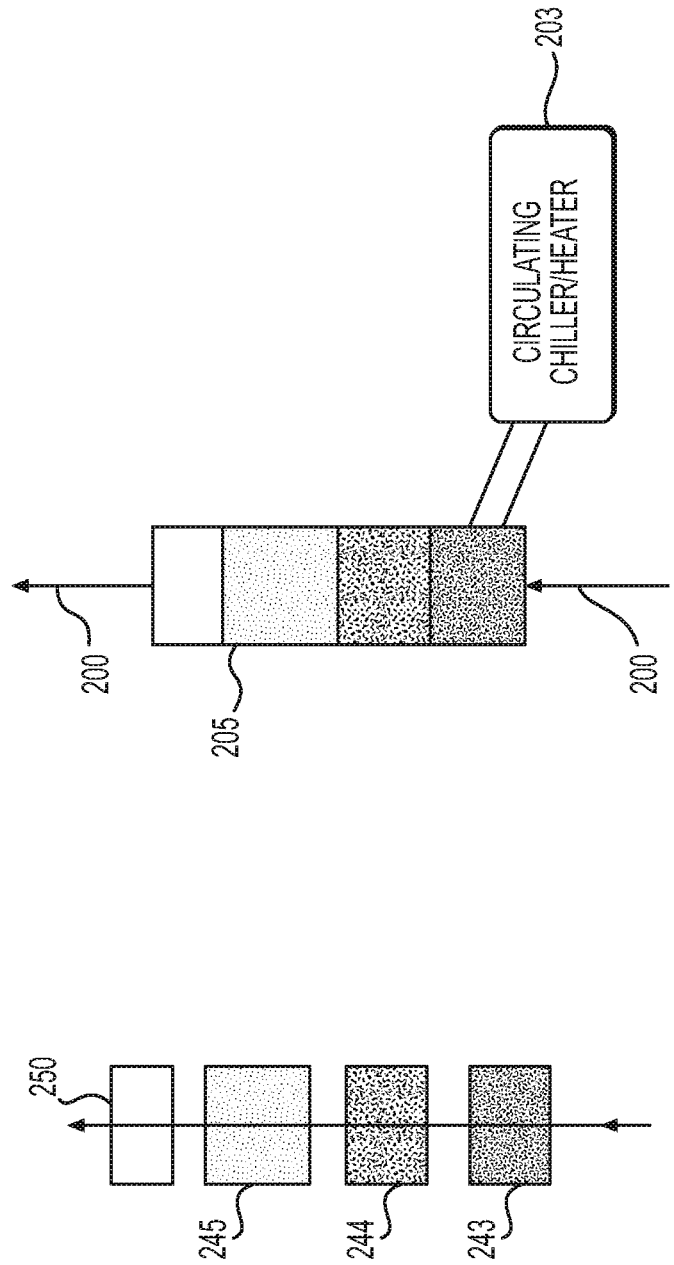
FIG. 28 shows a multistage molecular sieve and separated stages.

FIG. 28 shows a multistage molecular sieve and separated stages. Circulating gases 200 flow through multistage sieve 205. Stages 243, 244, 245 and 246 are separated.

Figure 29:
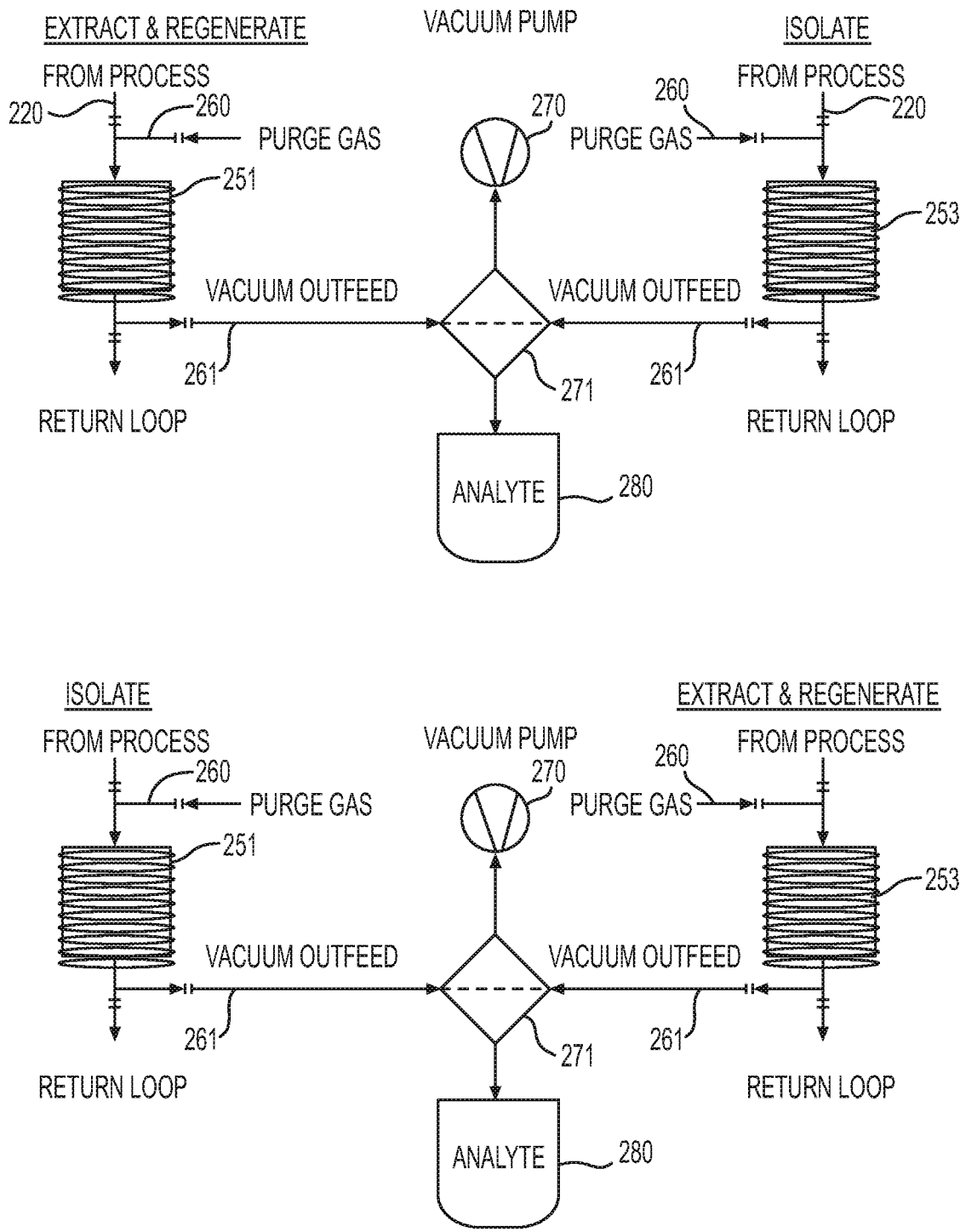
FIG. 29 shows recovery of the product—the analyte from the molecular sieve by alternating cycle of isolation and extraction/regeneration for continuous process operation.

FIG. 29 shows recovery of the product—the analyte from the molecular sieve by alternating cycle of isolation and extraction/regeneration for continuous process operation. Alternate cycle extraction and regeneration are shown by stopping (thin lines) the purge gas and vacuuming 261 with a vacuum pump 270 the purge gas with analyte through a vacuum filter 271 and collecting the analyte 280. The upper drawing shows recovery of the analyte from a cryo processor at the left while continuing the cryo processing in a cryo processor at the right. The reverse is shown in the lower drawing.

Figure 30:
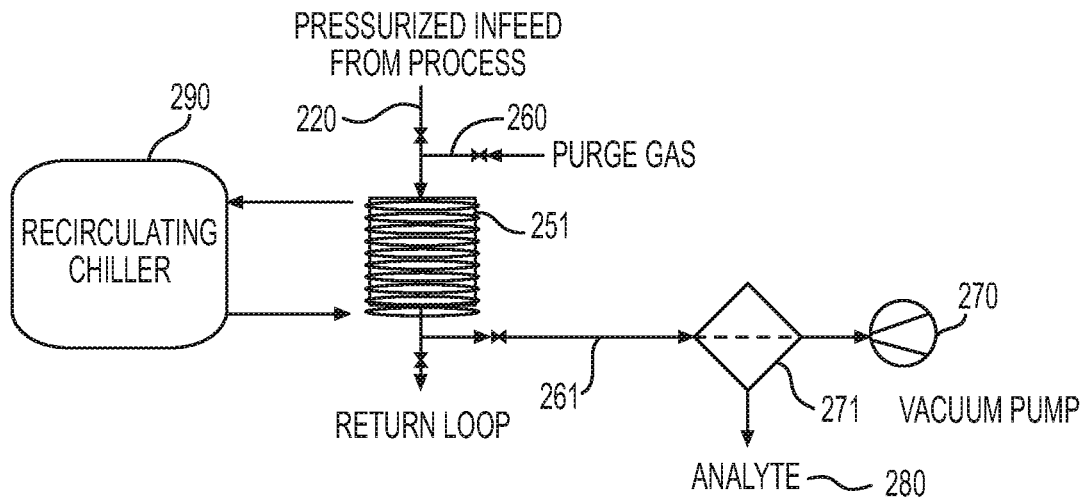
FIG. 30 shows apparatus to isolate and extract an analyte from a molecular sieve using a recirculating chiller.

FIG. 30 shows apparatus to isolate and extract an analyte from a molecular sieve using a recirculating chiller.

Figure 31:
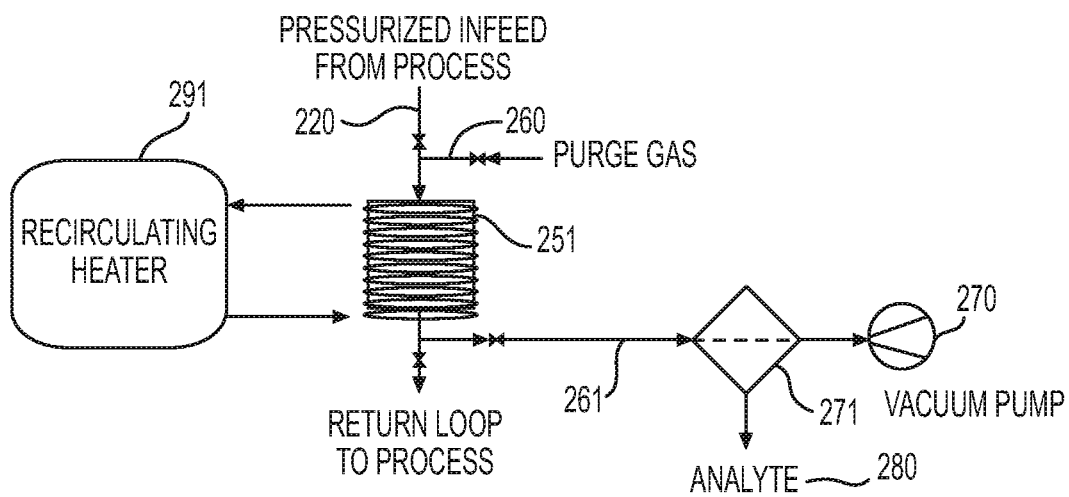
FIG. 31 shows apparatus to isolate and extract an analyte from a molecular sieve using a recirculating heater.

FIG. 31 shows apparatus to isolate and extract an analyte from a molecular sieve using a recirculating heater.

Figure 25:
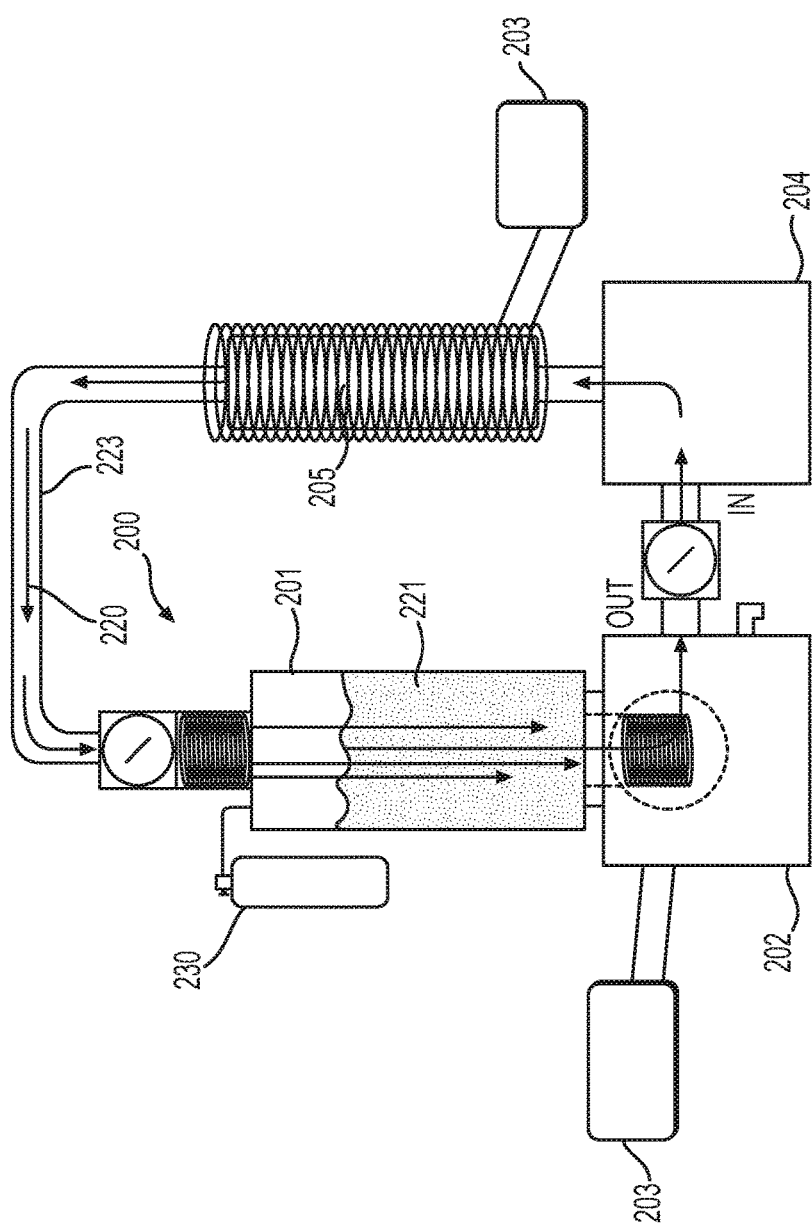
FIG. 25 schematically shows a down flow CryoCure system.

FIG. 30 shows the processing continuing with the purge gas 260 and the vacuum line 261 valved off. The recirculating chiller 290, 203 in FIGS. 25 and 27, operates during the processing with the circulating gas 220 through the molecular sieve 251.

When gas 220 is turned off, recirculating chiller 290 is replaced by a recirculating heater 291 while the purge gas 260 flows through molecular sieve 251 and vacuum pump 270 draws the analyte enriched purge gas through the vacuum outfeed 261 and the vacuum filter 271 to separate and collect the analyte 280.

Dispensing & Labeling of Topical and Edible Products

Topical & Edible products are manufactured from recipes and because of the difficulty involved, do not carry lot information. The processes described elsewhere herein can also be applied to topical and edible products.

Different strains of agricultural products produce different cannabinoids.

Human bodies have endo-cannabinoids that react differently to distinct phyto-cannabinoids. Universal product codes such as barcodes with unique serial numbers on each container can bring up genetics of each product, what species, where it was grown, the processing history and participants of experiments in their results.

Cannabis Information Access System and Authenticate Track & Trace Methods

Systems exist for tracking cannabis from seed to sale through the use of cultivation lot numbers, radio frequency tags and/or barcodes. These cultivation lot numbers are used for regulatory purposes to track plants and plant materials from seed, to sale. Cannabis is sold and consumed as "flower" (aka "bud"), which is smoked, or as edible, topical, or vaped products. The most efficient method of manufacturing edible, topical and vaped cannabis products is through the use of essential oil extracts. Sometimes the extracts are made from a whole plant and sometimes from the trim, and even the waste. Sometimes the extracts are made from one cultivation lot but most commonly they are made from mixed lots. When this happens, it is difficult, if not impossible, for the extract based cannabis product to carry a meaningful cultivation lot number.

Although cultivation lots are used mainly for regulatory and material control purposes, each cultivation lot could also be used to record the bio history of the plant including, among other things: it's DNA, strain origins, genetic history, nutrient history, spectral history, as well as, related test data on contaminants and it's phyto-cannabinoid profile. (There are over 100 different phyto-cannabinoids present in varying amounts within cannabis plants that make up the cannabinoid profile and each has an associated pattern of effects on humans & other animals.

The effects of cannabinoids on humans and other animals are highly complex and personal in nature. Each person has a unique set of endo-cannabinoid receptors and each human body produces a unique set of endo-cannabinoids in varying amounts. The levels of these cannabinoids is called the endo-cannabinoid profile. The endo-cannabinoid receptors and endo-cannabinoid profile make up the human endo-cannabinoid system. The endo-cannabinoid system is involved in a wide range of physiological processes. There are some scientific researchers who suggest that who we are as humans, both physically and mentally, is largely influenced by our endo-cannabinoid system.

The human endo-cannabinoid system can be supplemented with phyto-cannabinoids from cannabis plants. The supplementation method can be by inhalation, ingestion, or absorption. The endo-cannabinoid receptors in each human's brain responds uniquely when supplemented by phyto-cannabinoids. The method of supplementation has significant effect on the physiology of the response.

Each phyto-cannabinoid has different effects on humans and these effects work in concert with each other in what is referred to as the entourage effect. Each cultivation lot of cannabis has a unique phyto-cannabinoid profile based upon the strain of the plant and it's bio history.

To add to the complexity, immediately after harvest the phyto-cannabinoid profile begins to change due to exposure to spectral energy of all frequencies, environmental conditions, and time. Methods employed in production and supplementation methods also effect the cannabinoids delivered to the patient, the amounts of each absorbed, the rate of absorption, and ultimately, its effects on the patient's experience. In addition, these effects can be affected by drug interactions as well as by other compounds added to extract based products such as caffeine, alcohol, and sugar which are added to edible products.

Due to the complexity and personal nature of cannabis selection and dosing there is currently no system that effectively prescribes strains, not to mention lots of cannabis, or cannabis products to patients. This leaves each patient, sometimes with $3^{rd}$ party help from others, the responsibility to manage their selection of strains, methods of supplementation, and dosage amounts. For a patient/consumer to get the desired effects they need an easy source of reference information, experiential information, and an easy way track their experiences.

A "vintage" in the world of wine is defined as "the year a wine was produced".

The coined term "canntage" is defined as the bio, production and experiential history of an extract based product and/or the producer's narrative description of a production lot of an extract based product and where each production lot is assigned unique identifying canntage number and each packaged product may also be assigned a Unique Identification Code (UIC) associated to the canntage number from which it came.

Therefore, the new system provides:
1. that the canntage information on a production lot of cannabis products be assigned a canntage number,
2. that individual packaged products be marked with a unique identification code (UIC) that is associated in a database to its source canntage,
3. that a UIC be imprinted on each packaged cannabis product, using when possible a machine readable method e.g. barcode, rf tag
4. that canntage information be added to a database to associate the UIC with its canntage,
5. that canntage information be accessed by scanning the UIC imprint with a "smart" device, e.g. a smart phone,
6. that an application in the smart device would allow access to canntage information,
7. access to canntage information is through a website or app,
8. that access could be restricted to registered members of the website, or through an information service,
9. that registered members could add experiential to the canntage database,
10. that provide registered members a canntage journal to record their experiences,
11. that canntage journal databases could be data mined by deep learning algorithms to provide information to help members manage selection and dosage,
12. that registered members could allow anonymous data mining of experiential information as source information for deep learning algorithms,
13. that adding information on a UIC could be restricted to one registered member and/or,
14. that creates easy access to other related linked databases or websites containing referential information.

In the new system and method of doing business:
1. packed cannabis products carry a UIC,
2. package is defined herein as "any type of cartridge, container, carton or wrapping used to carry an extract based product" and packaged is defined as "filling, dispensing, or loading an extract based into a container",
3. a package is pre-imprinted with the UIC, sold and registered to a producer,
4. a UIC is issued and registered to a producer for them to imprint,
5. canntage information is added to the data base when the product is packaged,
6. producers can use to the database to market their products, 7. members can access the database to manage their selection and dosage of products and record comments and experiential information, and/or:
8. revenue is derived from:
   a. membership fees,
   b. sale of enabling products, such as packaging equipment and supplies
   c. use of UICs,
   d. administrative fees,
   e. licensing,
   f. advertising, and/or
   g. affiliate fees and commissions.

The new method and system authenticate, track and trace products containing extract based products where:
1. a UIC is registered to a producer,
2. a UIC is authenticated and verified for use by a producer,
3. a UIC is imprinted on packaged products,
4. a UIC is linked to a registered user
5. UIC relevant information is added to a canntage database,
6. the information can be accessed by members and producers, and/or
7. the information can be used for regulatory compliance.

In other applications of the invention, the new process system and method is applicable to all products whether ingested, applied, assembled or used in other products where product safety and distribution are important.

Figure 32:
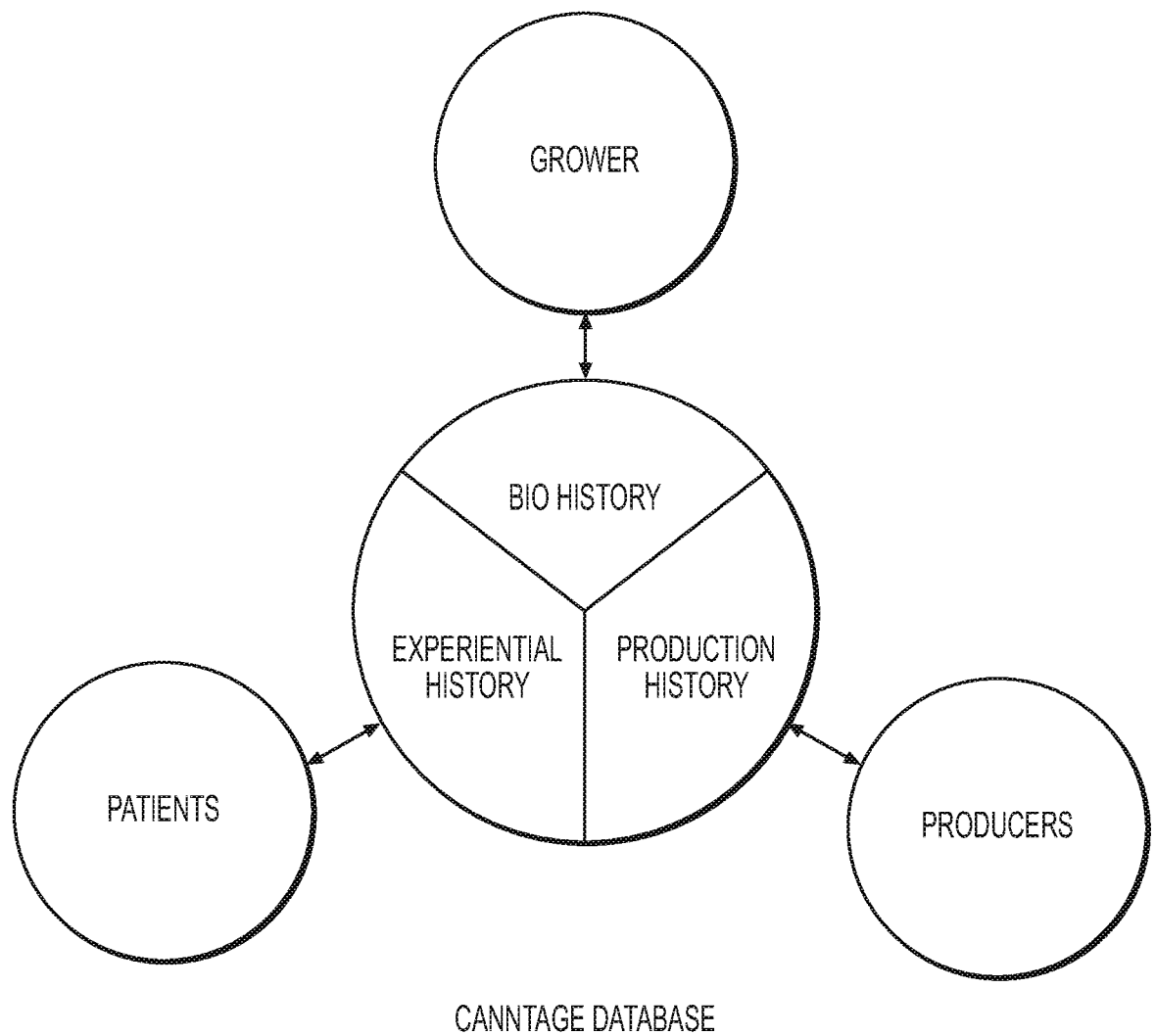
FIG. 32 shows the grower, the bio history of the raw material, the production history and producers of each product and the experiment history and the participants.
Figure 33:
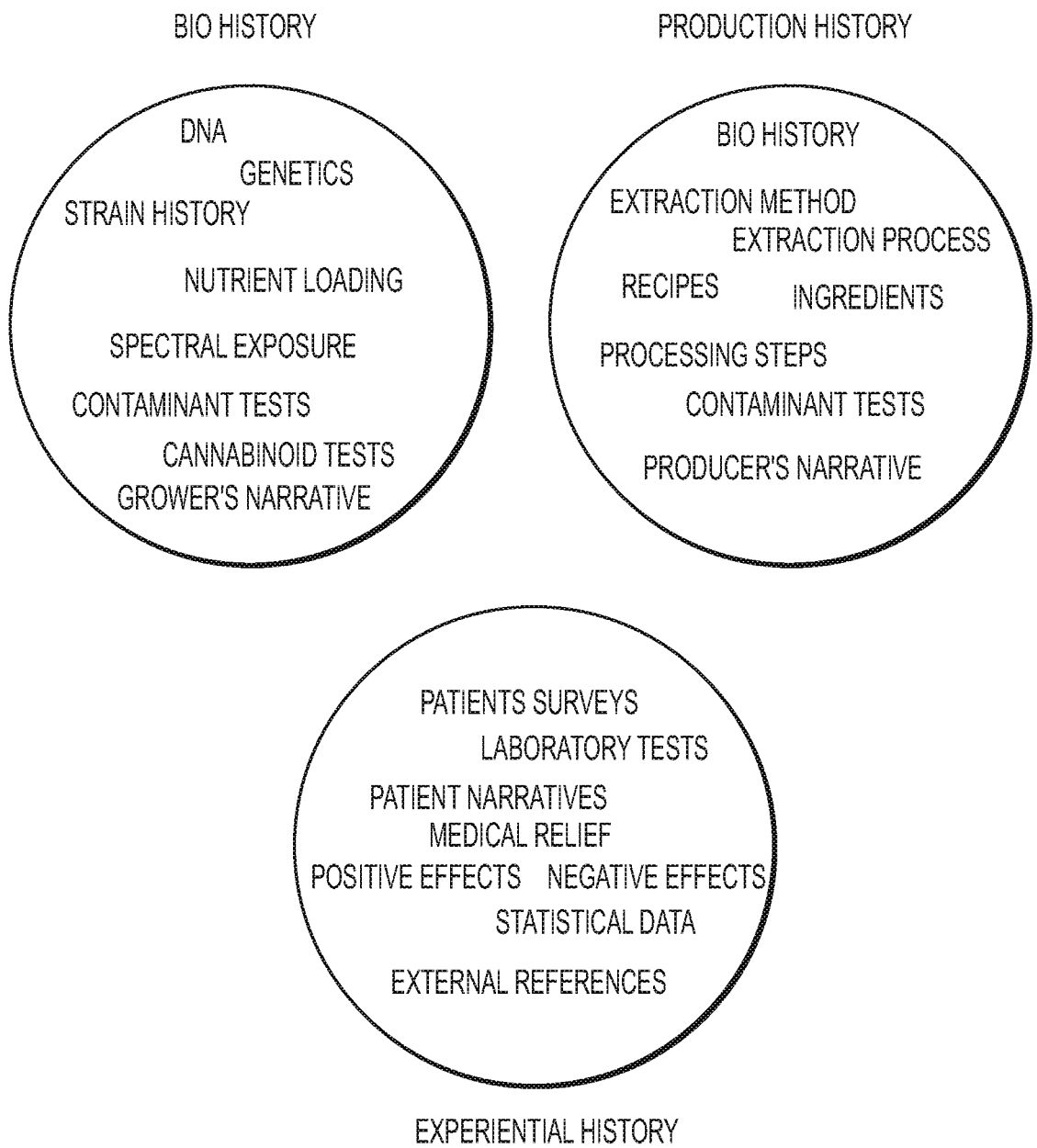
FIG. 33 shows the factors that are included in the bio history, the production history and the experimental history of each product.

FIGS. 32 and 33 show the history that is recorded for each product.

FIG. 32 shows the grower, the bio history of the raw material, the production history and producers of each product and the experiment history and the participants.

FIG. 33 shows the factors that are included in the bio history, the production history and the experimental history of each product.

Figures 34, 36, 37:
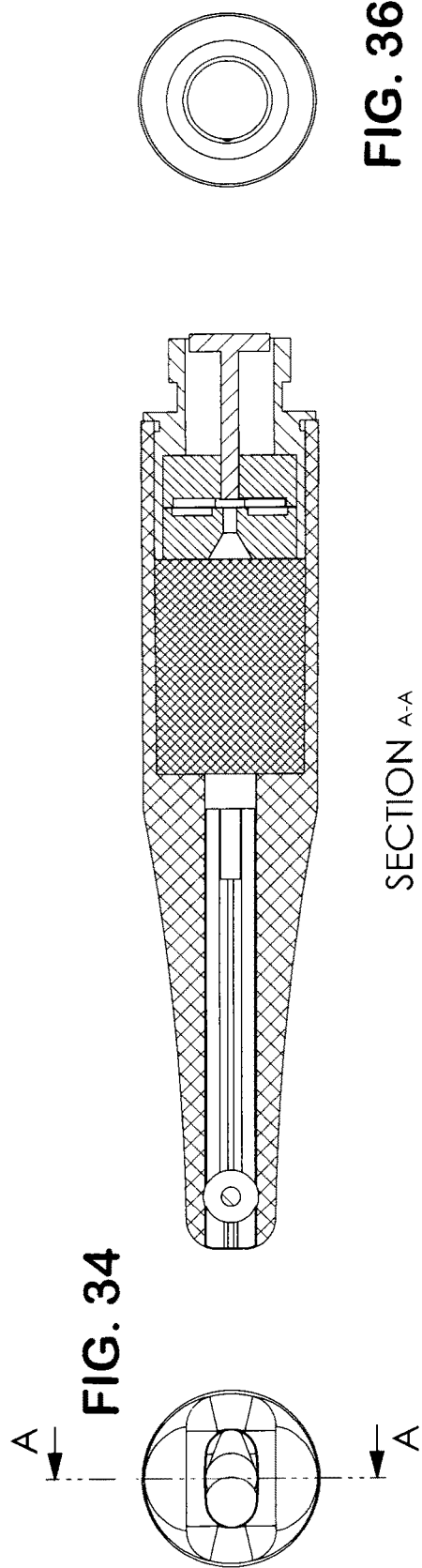
FIG. 34 is an end view of a new vapor cartridge.
FIG. 36 is an opposite end view of the vapor cartridge shown in FIGS. 34 and 35.
FIG. 37 is an end view rotated 90° of the vapor cartridge shown in FIGS. 34-36.

FIG. 34 is an end view of a new vapor cartridge.

FIG. 35 is a cross-sections view of the vapor cartridge taken along line A-A of FIG. 34.

FIG. 36 is an opposite end view of the vapor cartridge shown in FIGS. 34 and 35.

FIG. 37 is an end view rotated 90° of the vapor cartridge shown in FIGS. 34-36.

FIG. 38 is a cross-sectional elevation of the vapor cartridge taken along line B-B in FIG. 37.

Figure 39:
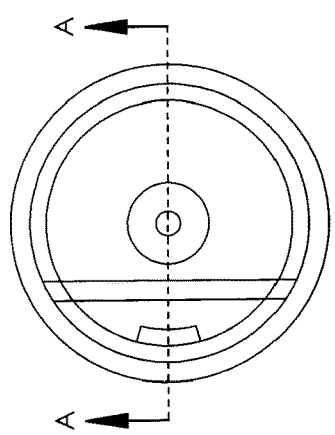
FIG. 39 is an inner end elevation of the vapor cartridge control insert.

FIG. 39 is an inner end elevation of the vapor cartridge control insert.

Figure 40:
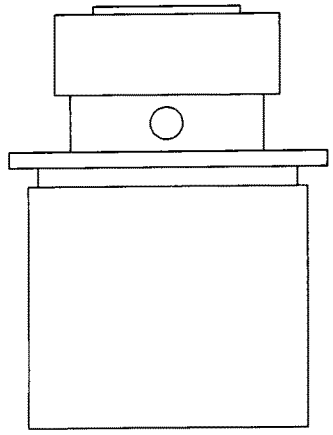
FIG. 40 is a side elevation of the vapor cartridge control insert shown in FIG. 39.

FIG. 40 is a side elevation of the vapor cartridge control insert shown in FIG. 39.

Figure 41:
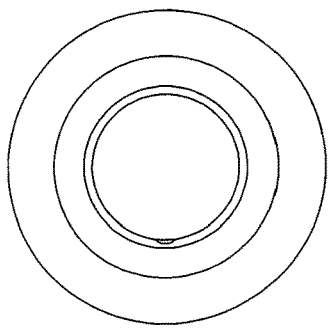
FIG. 41 is an outer end view of the vapor cartridge control insert.

FIG. 41 is an outer end view of the vapor cartridge control insert.

Figure 42:
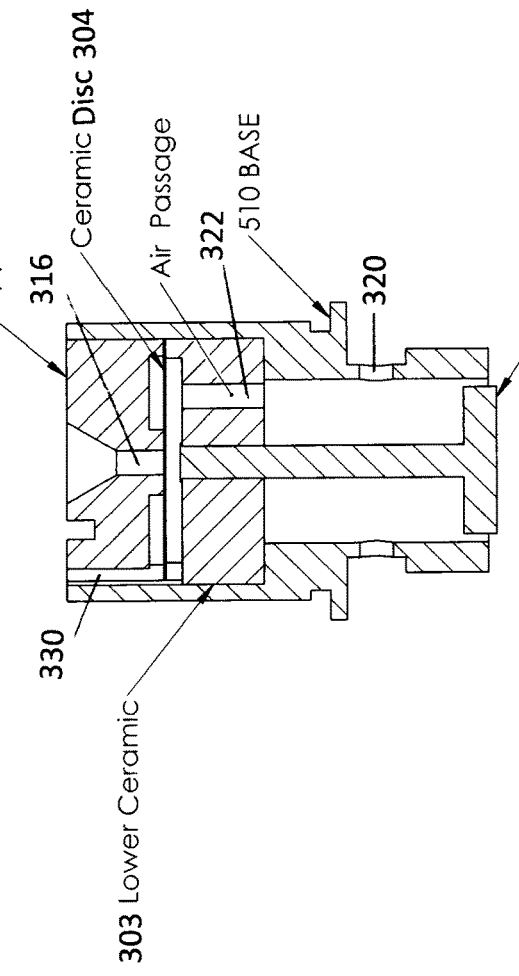
FIG. 42 is a cross-sectional view of the vapor cartridge control insert taken along line A-A of FIG. 39.

FIG. 42 is a cross-sectional view of the vapor cartridge control insert taken along line A-A of FIG. 39.

Figure 43:
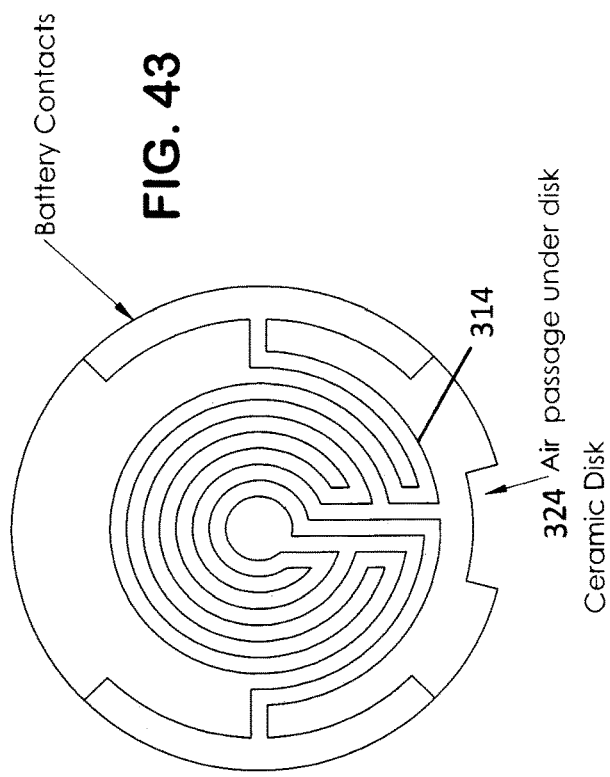
FIG. 43 is an enlarged outer side view of the vapor cartridge control insert ceramic disc.

FIG. 43 is an enlarged outer side view of the vapor cartridge control insert ceramic disc.

The latest vape cartridge construction 300 has a preferably clear, one piece integral plastic reservoir and mouthpiece 301, threaded battery mount 302, lower ceramic insulator 303 with air/vapor passages, ceramic disc 304 with printed heater coil which acts as both a valve and a vaporizer, ball 305 to seal the fill passage after filling, fill and vape passage 306 and vape passage 307.

This simplified vape cartridge is composed of seven components compared to current vape cartridges which total seventeen or more components, Current vape cartridges have chronic problems with leakage. One feature of this new construction is the small ceramic heater disc 304 made from flexible ceramic. The thin disc 304 is deformed by the negative vapor pressure of the disc, so that when it heats up it causes the disc to dome, opening the valve that allows the oil in the reservoir to flow onto the heated disc and vaporize.

The reservoir 310 is filled by pushing the ball 305 aside and inserting a needle through the fill and vape passage 306 and into the reservoir 310. The drawn breath deflects the disc 304 to complete a circuit with the battery contact 312. The heater electrode pattern 314 on the thin disc domes the disc. Heating the disc 304 domes the disc, opening the reservoir passage 316 to allow the vapor to flow toward the disc, heating the vapor and mixing it with the air coming in through openings 320 and passages 322 and 324. Mixed vapor and drawn in air moves through the vape passages 330, 307 and 306. Each successive indrawn air pulls the thin disc 304 into contact with a battery connection, completing the heater circuit and heating and doming the disc, opening the reservoir passage and heating vapor and air moving across the disc.

While the invention has been described with reference to specific embodiments, modifications and variations of the invention may be constructed without departing from the scope of the invention, which is defined in the following claims.

I claim:

1. Apparatus comprising:
   a system for processing botanical source materials, extracting oils, further comprising:
   a freezing column adapted for freezing, comminuting and sublimating fluids from botanical source materials,
   a batch hopper for loading botanical materials into the column,
   a cold gas source connected to a gas inlet near a bottom of the freezing column,
   a filter positioned in the freezing column above the gas inlet,
   a movable blade or whip mounted above the filter adapted for comminuting the bio source material above the filter,
   an outlet near the lip of the freezing column,
   sight glasses in the column adapted for observing the bio source materials in the column,
   a particle hopper connected to the outlet,
   a cyclone separator connected to the particle hopper,
   a particle collection container connected to the cyclone separator,
   a trapping filter connected to the cyclone separator adapted for dropping particles into the collection container,
   a gas a vapor outlet connected to the trapping filter, and
   a gas and vapor processing unit connected to the gas and vapor outlet.

2. The apparatus of claim 1, wherein the gas and vapor processing unit further comprises:
   a cold trap connected to the gas and vapor outlet,
   a coalescing filter connected to the cold trap,
   a circulating pump compressor connected to the coalescing filter, and
   a back pressure valve connected to the circulating pump compressor and connected to the gas inlet near the bottom of the column.

3. The apparatus of claim 1, further comprising:
a hygrometer connected to the freezing column,
a vacuum pump connected to the hygrometer and adapted for maintaining a low pressure in the freezing column,
a mixing valve connected to the gas inlet near the bottom of the column,
a liquid source connected to the dryer,
a dryer connected to the mixing valve, and
a pressure controller connected to the freezing column and to the vacuum pump and adapted for controlling pressure in the freezing column.

4. The apparatus of claim 1, wherein the gas and vapor processing unit further comprises a winterizing and filtering apparatus having:
a container,
a stirrer in the container,
a temperature sensor connected to the container,
a chiller surrounding the container,
a pump having an input to the container and having an output connected to a line returning liquid material,
a filter connected to the line for filtering the liquid material before returning the liquid material to the container,
an inlet connected to the container and adapted for admitting a liquid material to the container,
a solvent inlet connected to the container and adapted for admitting solvent to the container,
a distiller connected to the container and adapted for removing solvent gas from the container and collecting solvent distilled from the gas,
a product outlet connected to the container,
a filter connected to the product outlet, and
a flask connected to the filter and configured receiving product after solvent has been removed.

5. The apparatus of claim 4, further comprising a cartridge filter adapted for connection to and filing from the flask.

6. The apparatus of claim 5, comprising a cartridge hopper connected to the cartridge filler and a cartridge handler connected to the cartridge hopper and to the cartridge filler and adapted for providing individual cartridges to the cartridge filler, and a cartridge printer connected to the cartridge handler and adapted for printing information on each cartridge or on a label attached to each cartridge.

7. The apparatus of claim 6, further comprising a scanner connected to the cartridge printer for scanning information to be printed on the cartridges with the cartridge printed.

8. The apparatus of claim 6, wherein the printer is adapted to print source DNA genetics strain history, nutrient loading spectral exposure containment test and growers narrative on the cartridges or cartridge labels.

9. The apparatus of claim 6, wherein the printer is adapted to print bio-history extraction method, extraction process and producers' narrative on the cartridges or cartridge labels.

\* \* \* \* \*